United States Patent
Mori et al.

(10) Patent No.: US 11,472,867 B2
(45) Date of Patent: Oct. 18, 2022

(54) ANTI-HSV GB MONOCLONAL ANTIBODY OR ANTIGEN-BINDING FRAGMENT THEREOF

(71) Applicant: KM Biologies Co., Ltd., Kumamoto (JP)

(72) Inventors: Hiroaki Mori, Kumamoto (JP); Tomohiro Nishimura, Kumamoto (JP); Hiroyuki Shimizu, Ageo (JP); Akihiro Koube, Kikuyo-machi (JP)

(73) Assignee: KM BIOLOGICS CO., LTD., Kumamoto (JP)

( * ) Notice: Subject to any disclaimer, the term of this patent is extended or adjusted under 35 U.S.C. 154(b) by 143 days.

(21) Appl. No.: 16/641,408

(22) PCT Filed: Aug. 29, 2018

(86) PCT No.: PCT/JP2018/032019
§ 371 (c)(1),
(2) Date: Feb. 24, 2020

(87) PCT Pub. No.: WO2019/044926
PCT Pub. Date: Mar. 7, 2019

(65) Prior Publication Data
US 2020/0239549 A1 Jul. 30, 2020

(30) Foreign Application Priority Data
Aug. 30, 2017 (JP) .............................. JP2017-165968

(51) Int. Cl.
C07K 16/08 (2006.01)
A61P 31/22 (2006.01)
C07K 16/46 (2006.01)
A61K 39/00 (2006.01)

(52) U.S. Cl.
CPC ............ *C07K 16/087* (2013.01); *A61P 31/22* (2018.01); *C07K 16/461* (2013.01); *A61K 2039/505* (2013.01); *C07K 2317/24* (2013.01); *C07K 2317/51* (2013.01); *C07K 2317/515* (2013.01); *C07K 2317/55* (2013.01); *C07K 2317/565* (2013.01); *C07K 2317/622* (2013.01)

(58) Field of Classification Search
CPC ................ C07K 16/087; C07K 16/461; C07K 2317/24; C07K 2317/51; C07K 2317/515; C07K 2317/55; C07K 2317/565; C07K 2317/622; C07K 2317/21; C07K 2317/34; C07K 2317/76; C07K 2317/92; A61P 31/22; A61K 2039/505; C12N 5/10; C12N 15/09

See application file for complete search history.

(56) References Cited

U.S. PATENT DOCUMENTS 6,156,313 A 12/2000 Burton et al.

FOREIGN PATENT DOCUMENTS

| JP | 2013-506403 A | 2/2013 |
| JP | 2017-520572 A | 7/2017 |
| WO | 2011/038933 A2 | 4/2011 |
| WO | 2015/197763 A1 | 12/2015 |

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*
Kussie PH, Parhami-Seren B, Wysocki LJ, Margolies MN. A single engineered amino acid substitution changes antibody fine specificity. J Immunol. Jan. 1, 1994;152(1): 146-52. (Year: 1994).*
Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714. (Year: 2015).*
Sela-Culang I, Kunik V, Ofran Y. The structural basis of antibody-antigen recognition. Front Immunol. Oct. 8, 2013;4:302. (Year: 2013).*
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2015).*
Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*
Collis AV, Brouwer AP, Martin AC. Analysis of the antigen combining site: correlations between length and sequence composition of the hypervariable loops and the nature of the antigen. J Mol Biol. Jan. 10, 2003;325(2):337-54. (Year: 2003).*

(Continued)

*Primary Examiner* — Rachel B Gill
(74) *Attorney, Agent, or Firm* — Pillsbury Winthrop Shaw Pittman LLP

(57) ABSTRACT

An anti-HSV monoclonal antibody or an antigen-binding fragment thereof is an anti-HSV gB monoclonal antibody or an antigen-binding fragment thereof that specifically binds to herpes simplex virus (HSV) envelope glycoprotein B (gB), comprising: a heavy chain variable region comprising a heavy chain CDR1 consisting of the amino acid sequence set forth in SEQ ID NO: 3, a heavy chain CDR2 consisting of the amino acid sequence set forth in SEQ ID NO: 4, and a heavy chain CDR3 consisting of the amino acid sequence set forth in SEQ ID NO: 5; and a light chain variable region comprising a light chain CDR1 consisting of the amino acid sequence set forth in SEQ ID NO: 6, a light chain CDR2 consisting of the amino acid sequence set forth in SEQ ID NO: 7, and a light chain CDR3 consisting of the amino acid sequence set forth in SEQ ID NO: 8.

12 Claims, 13 Drawing Sheets
Specification includes a Sequence Listing.

(56) References Cited

OTHER PUBLICATIONS

Dondelinger M, Filée P, Sauvage E, Quinting B, Muyldermans S, Galleni M, Vandevenne MS. Understanding the Significance and Implications of Antibody Numbering and Antigen-Binding Surface/Residue Definition. Front Immunol. Oct. 16, 2018;9:2278. (Year: 2018).*

Ahmadzadeh V, Farajnia S, Feizi Mah, Nejad Rak. Antibody humanization methods for development of therapeutic applications. Monoclon Antib Immunodiagn Immunother. (2014) 33:67-73. (Year: 2014).*

Kunik V, Peters B, Ofran Y. Structural consensus among antibodies defines the antigen binding site. PLoS Comput Biol. 2012;8(2): e1002388. Epub Feb. 23, 2012. (Year: 2012).*

Apgar JR, Mader M, Agostinelli R, Benard S, Bialek P, Johnson M, Gao Y, Krebs M, Owens J, Parris K, St Andre M, et. al. Beyond CDR-grafting: Structure-guided humanization of framework and CDR regions of an anti-myostatin antibody. MAbs. Oct. 2016;8(7): 1302-1318. Epub Sep. 13, 2016. (Year: 2016).*

Patent Cooperation Treaty, International Search Report issued in PCT/JP2018/032019, dated Oct. 2, 2018, pp. 1-2.

Patent Cooperation Treaty, International Preliminary Report on Patentability issued in PCT/JP2018/032019, dated Oct. 2, 2018, pp. 1-7.

Roizman, et al., "Fields Virology 5th ed., Herpes simplex viruses", 2007, pp. 2501-2569, Lippincott Williams & Wilkins, Philadelphia, PA.

Hashido, et al., "An epidemiologic study of herpes simplex virus type 1 and 2 infection in Japan based on type-specific serological assays", Epidemiol Infect., Mar. 1998, pp. 179-186, vol. 120(2).

Kawaguchi, "Herpes simplex virus (HSV)", Virus, 2010, p. 187-p. 196, vol. 60(2), partial translation.

Herold, et al., "Glycoprotein C-independent binding of herpes simplex virus to cells requires cell surface heparan sulphate and glycoprotein B.", J Gen Virol, 1994, pp. 1211-1222, 75 (Pt 6).

Herold, et al., "Glycoprotein C of herpes simplex virus type 1 plays a principal role in the adsorption of virus to cells and in infectivity.", J Virol, 1991, pp. 1090-1098, 65(3).

Arii, et al., "Non-muscle myosin IIA is a functional entry receptor for herpes simplex virus-1.", Nature, 2010, pp. 859-862, vol. 467.

Satoh, et al., "PILRalpha is a herpes simplex virus-1 entry coreceptor that associates with glycoprotein B.", Cell, 2008, pp. 935-944, vol. 132.

Suenaga, et al., "Myelin-associated glycoprotein mediates membrane fusion and entry of neurotropic herpesviruses.", Proc Natl Acad Sci USA, 2010, pp. 866-871, vol. 107.

Geraghty, et al., "Entry of alphaherpesviruses mediated by poliovirus receptor-related protein 1 and poliovirus receptor.", Science, 1998, pp. 1618-1620, vol. 280.

Montgomery, et al., "Herpes simplex virus-1 entry into cells mediated by a novel member of the TNF/NGF receptor family.", Cell, 1996, pp. 427-436, vol. 87.

Shukla, et al., "A novel role for 3-O-sulfated heparan sulfate in herpes simplex virus 1 entry.", Cell, 1999, pp. 13-22, vol. 99.

Eisenberg, et al., "Herpes virus fusion and entry: a story with many characters ", Viruses, 2012, pp. 800-832, vol. 4.

Pottage, Jr., et al., "Herpes simplex virus resistance to acyclovir: clinical relevance.", Infect Agents Dis., Sep. 1995, pp. 115-124, vol. 4(3).

Krawczyk, et al., "Impact of valency of a glycoprotein B-specific monoclonal antibody on neutralization of herpes simplex virus.", J Virol., Feb. 2011, pp. 1793-1803, vol. 85(4).

Bender, et al., "Antigenic and mutational analyses of herpes simplex virus glycoprotein B reveal four functional regions", J. Virol., 2007, pp. 3827-3841, vol. 81.

Heldwein, et al., "Crystal structure of glycoprotein B from herpes simplex virus 1", Science, 2006, pp. 217-220, vol. 313.

Sanchez-Pescador, et al., "Epitopes of herpes simplex virus type 1 glycoprotein B that bind type-common neutralizing antibodies elicit type-specific antibody-dependent cellular cytotoxicity", The Journal of infectious diseases, 1992, pp. 623-627, vol. 166.

Pereira, et al., "Domain structure of herpes simplex virus 1 glycoprotein B: neutralizing epitopes map in regions of continuous and discontinuous residues", Virology, 1989, pp. 11-24, vol. 172.

Qadri, et al., "Mutations in conformation-dependent domains of herpes simplex virus 1 glycoprotein B affect the antigenic properties, dimerization, and transport of the molecule", Virology, 1991, pp. 135-152, vol. 180.

Navarro, et al., "Domains of herpes simplex virus I glycoprotein B that function in virus penetration, cell-to-cell spread, and cell fusion", Virology, 1992, pp. 99-112, vol. 186.

Cairns, et al., "Dissection of the antibody response against herpes simplex virus glycoproteins in naturally infected humans", J. Virol, 2014, pp. 12612-12622, vol. 88.

Chauhan, et al., "Identification of broadly reactive epitopes targeting major glycoproteins of Herpes simplex virus (HSV) 1 and 2—An immunoinformatics analysis", Infect. Genet. Evol., Mar. 7, 2018, pp. 24-35, vol. 61.

* cited by examiner

Fig.13

```
HSV1   :MHQGAPSWGRRWFVVWALLGLTLGVLVASAAPTSPGTP----GVAAATQAANGGPATPAPP  27
HSV2   :MRGGGLICALVVGALVAAVASA--------APAAPAAPRASGGVAATVAANGGPASRPPP  30

HSV1  28:PLGAAPTGDPKPKKNKKPKNPTPPRPAGDNATVAAGHATLREHLRDIKAENTDANFYVCP  87
HSV2  31:VPSPATTKARKRKTKKPPKRPEATPPPDANATVAAGHATLRAHLREIKVENADAQFYVCP  90

HSV1  88:PPTGATVVQFEQPRRCPTRPEGQNYTEGIAVVFKENIAPYKFKATMYYKDVTVSQVWFGH 147
HSV2  91:PPTGATVVQFEQPRRCPTRPEGQNYTEGIAVVFKENIAPYKFKATMYYKDVTVSQVWFGH 150

HSV1 148:RYSQFMGIFEDRAPVPFEEVIDKINAKGVCRSTAKYVRNNLETTAFHRDDHETDMELKPA 207
HSV2 151:RYSQFMGIFEDRAFVPFEEVIDKINAKGVCRSTAKYVRNNMETTAFHRDDHETDMELKPA 210

HSV1 208:NAATRTSRGWHTTDLKYNPSRVEAFHRYGTTVNCIVEEVDARSVYPYDEFVLATGDFVYM 267
HSV2 211:KVATRTSRGWHTTDLKYNPSRVEAFHRYGTTVNCIVEEVDARSVYPYDEFVLATGDFVYM 270

HSV1 268:SPFYGYREGSHTEHTTYAADRFKQVDGFYARDLTTKARATAPTTRNLLTTPKFTVAWDWV 327
HSV2 271:SPFYGYREGSHTEHTSYAADRFKQVDGFYARDLTTKARATSPTTRNLLTTPKFTVAWDWV 330

HSV1 328:PKRPSVCTMTKWQEVDEMLRSEYGGSFRFSSDAISTTFTTNLTEYPLSRVDLGDCIGKDA 387
HSV2 331:PKRPAVCTMTKWQEVDEMLRAEYGGSFRFSSDAISTTFTTNLTQYSLSRVDLGDCIGRDA 390

HSV1 388:RDAMDRIFARRYNATHIKVGQPQYYQANGGFLIAYQPLLSNTLAELYVREHLPEQSRKPP 447
HSV2 391:REAIDRMFARKYNATHIKVSQPQYYLATGGFLIAYQPLLSNTLAELYVREYMREQDRKPR 450

HSV1 478:NPTPPPF--GASANASVERIKTTSSIEFARLQFTYNHIQRHVNDMLGRVAIAWCELQNHE 505
HSV2 451:NATPAPLREAPSANASVERIKTTSSIEFARLQFTYNRIQRHVNDMLGRIAVAWCELQNHE 510

HSV1 506:LTLWNEARKLNPNAIASVTGRRVSARMLGDVMAVSTCVPVAADNVIVQNSMRISSRPGA 565
HSV2 511:LTLWNEARKLNPNAIASATVGRRVSARMLGDVMAVSTCVPVAPDNVIVQNSMRVSSRPGT 570

HSV1 566:CYSRPLVSFRYEDQGPLVEGQLGENNELRLTRDAIEPCTVGERRYFTFGGGYVYFEEYAY 625
HSV2 571:CYSRPLVSFRYEDQGPLTEGQLGENNELRLTRDALEPCTVGHRRYFTFGGGYVYFEEYAY 630

HSV1 626:SHQLSRADITTVSTFIDLNITMLEDHEFVPLEVYTRHEIKDSGLLDYTEVQRRNQLHDLR 685
HSV2 631:SHQLSRADVTTVSTFIDLNITMLEDHEFVPLEVYTRHEIKDSGLLDYTEVQRRNQLHDLR 690

HSV1 686:FADIDTVIHADANAAMFAGLGAFFEGMGDLGRAVGKVVMGIVGGVVSAVSGVSSFMSNPF 745
HSV2 691:FADIDTVIRADANAAMFAGLGAFFEGMGDLGRAVGKVVMGVVGGVVSAVSGVSSFMSNPF 750

HSV1 746:GALAVGLLVLAGLAAAFFAFRYVMRLQSNPMKALYPLTTKELKNPTNPDASGEGEE---G 802
HSV2 751:GALAVGLLVLAGLVAAFFAFRYVLQLQRNPMKALYPLTTKELKTSDPGGVGGEGEEGAEG 810

HSV1 803:GDFDEAKLAEAREMIRYMALVSAMERTEHKAKKKGTSALLSAKVTDMVMRKRRNTNYTQV 862
HSV2 811:GGFDEAKLAEAREMIRYMALVSAMERTEHKARKKGTSALLSSKVTNMVLRKRNKAPYSPL 870

HSV1 863:PNKDGDADEDDL                                             874
HSV2 871:HNEDEAGDEDEL                                             882
```

ANTI-HSV GB MONOCLONAL ANTIBODY OR ANTIGEN-BINDING FRAGMENT THEREOF

RELATED PATENT APPLICATIONS

This application is based on and claims the benefit of priority from International Application No. PCT/JP2018/032019, filed on Aug. 29, 2018, which claims priority to Japanese Patent Application No. 2017-0165968, filed on Aug. 30, 2017, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Feb. 21, 2020, is named "FP18-0826-00_Sequence_listing.txt" and is 20.4 KB in size.

TECHNICAL FIELD

The present invention relates to an anti-HSV gB monoclonal antibody or an antigen-binding fragment thereof.

BACKGROUND ART

Herpes simplex virus (HSV) is a neurotropic pathogen, moves to sensory nerves after the initial infection of mucosal epithelium, and establishes permanent latent infection in trigeminal ganglia or sacral ganglia. Latent HSVs are occasionally reactivated to cause various pathological conditions (Non-Patent Literature 1).

Two HSV serotypes (HSV-1, HSV-2) are known. HSV-1 is mainly responsible for herpes labialis and herpes keratitis and HSV-2 is mainly responsible for genital herpes. However, in recent years, due to the diversification of the sexual behavior, HSV-1 may often be responsible for genital herpes and HSV-2 may often be responsible for herpes labialis. The percentages of antibody-positive persons (previously infected persons) in Japan are 60 to 80% for HSV-1 and 10% for HSV-2 and, even for HSV-2 alone, the potential demand of vaccine is estimated to be 10000000 persons (Non-Patent Literature 2). Moreover, the percentages of antibody-positive persons (previously infected persons) in the United States are 57% for HSV-1 and 20% for HSV-2 (of which, about 10% is latent genital herpes) (Non-Patent Literature 3).

The establishment of infection of cells with HSV is known to involve 5 envelope glycoproteins in 2 phases, adsorption and entry. These 5 envelope glycoproteins are referred to as envelope glycoprotein B (gB), envelope glycoprotein C (gC), envelope glycoprotein D (gD), envelope glycoprotein H (gH), envelope glycoprotein L (gL) (Non-Patent Literature 4).

First the adsorption process is triggered by binding of gB and gC to heparan sulfate on the cell surface (Non-Patent Literature 5, 6). This process is not essential when HSV enters cells, but is considered to be involved in more efficient entry. Then, the entry process is initiated by the binding of gB and gD to respective host cell receptors and the fusion of the virus envelope and the host cell membrane.

Known host cell receptors include gB receptors and gD receptors. Identified gB receptors include NM-IIA (Non-Patent Literature 7, 8) and MAG (Non-Patent Literature 9). Identified gD receptors include Nectin 1 (Non-Patent Literature 10), HVEM (Non-Patent Literature 11), and 3-O-sulfated heparan sulfate (Non-Patent Literature 12). Moreover, the gH/gL heterodimer is known to interact with gB and gD and play an important role in the membrane fusion (Non-Patent Literature 13).

As a result of the determination of structure of HSV-1 gB in 2006, it was revealed that gB forms a trimer with 5 domains (Non-Patent Literature 14). Moreover, the structure of gB is a structure similar to that of gG in VSV (vesicular stomatitis virus), which is known as a membrane fusion protein, and this supports that gB is a membrane fusion protein in HSV. Moreover, gB is also highly conserved in other herpesvirus and considered that its function is shared among herpesviruses.

So far, analyses using mutants and monoclonal antibodies of gB have been performed in a plurality of groups to identify functional regions of HSV gB (Non-Patent Literature 15-18). As a result, several functional regions have been found.

Currently, antiviral drugs such as aciclovir are used in treatment of HSV, but they cannot remove the virus completely, and the virus is reactivated when the medication is discontinued. This is because HSV takes a special infection form referred to as latent infection to ganglia. Therefore, the development of a preventive vaccine for preventing infection itself with HSV or a therapeutic vaccine that alleviates or palliates symptoms of infection or symptoms of reactivation is desired, but there is currently no effective vaccine, with unmet needs for such a vaccine being high.

Moreover, there are concerns for increase of resistant virus strains caused by frequent or long-term use of antiviral drugs such as aciclovir and foscarnet (Non-Patent Literature 19). Furthermore, those antiviral drugs have various side effects such as liver dysfunction, spermatogenic dysfunction, gastrointestinal dysfunction, and kidney dysfunction and cases where drug reduction or drug withdrawal is unavoidable may occur.

HSV is known to be one of pathogens to which sufficient protective immunity cannot be acquired by a conventional vaccine or previous infection with a pathogen. This is considered to be because HSV has various immunoediting systems and cleverly avoids the immune reaction of the host.

CITATION LIST

Non Patent Literature

Non-Patent Literature 1: Roizman, B. et. al., Herpes simplex viruses, p. 2501-2602. In D. M. Knipe and P. M. Howley (ed.), "Fields Virology", 5th ed. Lippincott Williams &Wilkins, Philadelphia, Pa. 2007

Non-Patent Literature 2: Hashido M1 et. al., An epidemiologic study of herpes simplex virus type 1 and 2 infection in Japan based on type-specific serological assays, Epidemiol Infect. 1998 March; 120 (2): 179-86

Non-Patent Literature 3: Decision Resources; Emerging Vaccines 2008

Non-Patent Literature 4: Virus 2010, Vol. 60 (2), pp.187-196

Non-Patent Literature 5: Herold, B. C. et. al., Glycoprotein C-independent binding of herpes simplex virus to cells requires cell surface heparan sulphate and glycoprotein B. J Gen Virol 1994 75 (Pt 6): 1211-22

Non-Patent Literature 6: Herold, B. C. et. al., Glycoprotein C of herpes simplex virus type 1 plays a principal role in the adsorption of virus to cells and in infectivity. J Virol 1991 65: 1090-8

Non-Patent Literature 7: Arii, J. et. al., Non-muscle myosin IIA is a functional entry receptor for herpes simplex virus-1. Nature 2010 467:859-62

Non-Patent Literature 8: Satoh, T. et. al., PILRalpha is a herpes simplex virus-1 entry coreceptor that associates with glycoprotein B. Cell 2008 132:935-44

Non-Patent Literature 9: Suenaga, T. et. al., Myelin-associated glycoprotein mediates membrane fusion and entry of neurotropic herpesviruses. Proc Natl Acad Sci U S A 2010 107:866-71

Non-Patent Literature 10: Geraghty, R. J. et. al., Entry of alphaherpesviruses mediated by poliovirus receptor-related protein 1 and poliovirus receptor. Science 1998 280:1618-20

Non-Patent Literature 11: Montgomery, R. I. et. al., Herpes simplex virus-1 entry into cells mediated by a novel member of the TNF/NGF receptor family. Cell (1996) 87:427-36

Non-Patent Literature 12: Shukla, D., et. al., A novel role for 3-O-sulfated heparan sulfate in herpes simplex virus 1 entry. Cell 1999 99:13-22

Non-Patent Literature 13: Eisenberg RJ et. al., Herpes virus fusion and entry: a story with many characters. Viruses 2012 4:800-832 10.3390/v4050800

Non-Patent Literature 14: SCIENCE 2006 313, 14, 217-220

Non-Patent Literature 15: Virology 1989 172 (1), 11-24

Non-Patent Literature 16: Virology 1991 180 (1), 135-152

Non-Patent Literature 17: Virology 1992 186 (1), 99-112

Non-Patent Literature 18: Bender F C et. al., Antigenic and mutational analyses of herpes simplex virus glycoprotein B reveal four functional regions. J Virol. 2007 April 1981(8): 3827-41. Epub 2007 Jan. 31

Non-Patent Literature 19: Pottage J C Jr et. al., Herpes simplex virus resistance to acyclovir: clinical relevance. Infect Agents Dis. 1995 Sep. 4(3):115-24

Non-Patent Literature 20: Krawczyk A et. al., Impact of valency of a glycoprotein B-specific monoclonal antibody on neutralization of herpes simplex virus. J Virol. 2011 February;85(4):1793-803. doi: 10.1128/JVI.01924-10. Epub 2010 Dec. 1

SUMMARY OF INVENTION

Technical Problem

An object of the present invention is to provide a novel anti-HSV gB monoclonal antibody or an antigen-binding fragment thereof that exhibits HSV-neutralizing effect, suppresses intercellular transmission of HSV, and can be used in the prevention and/or treatment of HSV infection.

Solution to Problem

The present inventors obtained 44 anti-gB antibodies by comprehensive search of anti-HSV gB antibodies conducted by using a human antibody library. As a result of examining those antibodies in a virus neutralization test, it was found that the strain designated as monoclonal antibody D48 exhibits strong virus-neutralizing activity (plaque number-reducing activity) on HSV-1 and HSV-2 and intercellular transmission (cell to cell infection spread)-suppression activity and the intensity of the activity overwhelms those of other antibodies. The present inventors performed more detail analysis of monoclonal antibody D48, thereby completing the present invention.

Accordingly, the present invention relates to the following inventions.

(1) An anti-HSV gB monoclonal antibody or an antigen-binding fragment thereof that specifically binds to herpes simplex virus (HSV) envelope glycoprotein B (gB), comprising:

a heavy chain variable region comprising a heavy chain CDR1 consisting of the amino acid sequence set forth in SEQ ID NO: 3, a heavy chain CDR2 consisting of the amino acid sequence set forth in SEQ ID NO: 4, and a heavy chain CDR3 consisting of the amino acid sequence set forth in SEQ ID NO: 5; and a light chain variable region comprising a light chain CDR1 consisting of the amino acid sequence set forth in SEQ ID NO: 6, a light chain CDR2 consisting of the amino acid sequence set forth in SEQ ID NO: 7, and a light chain CDR3 consisting of the amino acid sequence set forth in SEQ ID NO: 8.

(2) The anti-HSV gB monoclonal antibody or antigen-binding fragment thereof according to the above (1), comprising: a heavy chain variable region comprising the amino acid sequence set forth in SEQ ID NO: 1 and a light chain variable region comprising the amino acid sequence set forth in SEQ ID NO: 2.

(3) The anti-HSV gB monoclonal antibody or antigen-binding fragment thereof according to the above (1) or (2), wherein the HSV is HSV-1 or HSV-2.

(4) A polynucleotide encoding the anti-HSV gB monoclonal antibody or antigen-binding fragment thereof according to any one of the above (1) to (3).

(5) An expression vector comprising the polynucleotide according to the above (4) and one or more regulatory sequences operably linked to the polynucleotide.

(6) A transformant comprising the expression vector according to the above (5) introduced therein.

(7) A method for producing the anti-HSV gB monoclonal antibody or antigen-binding fragment thereof according to any one of the above (1) to (3) using the polynucleotide according to the above (4), the expression vector according to the above (5), the transformant according to the above (6).

(8) A pharmaceutical composition for preventing or treating HSV infection, comprising the anti-HSV gB monoclonal antibody or antigen-binding fragment according to the above (1) or (2).

(9) The pharmaceutical composition according to the above (8), wherein the HSV infection is HSV-1 infection or HSV-2 infection.

(10) The pharmaceutical composition according to the above (8) or (9), wherein the HSV infection is selected from the group consisting of herpes labialis, herpetic keratitis, genital herpes, systemic neonatal herpes, and stomatitis, dermatosis, encephalitis, meningitis, and myelitis caused by HSV.

(11) An anti-HSV gB monoclonal antibody or an antigen-binding fragment thereof that specifically binds to at least one amino acid residue in the region consisting of the amino acid residues 383-388 of the herpes simplex virus-1 (HSV-1) envelope glycoprotein B (gB) set forth in SEQ ID NO: 10, and/or at least one amino acid residue in the region consisting of the amino acid residues 386-391 of the herpes simplex virus-2 (HSV-2) envelope glycoprotein B (gB) set forth in SEQ ID NO: 11.

(12) The anti-HSV gB monoclonal antibody or antigen-binding fragment thereof according to the above (11), comprising:

a heavy chain variable region comprising a heavy chain CDR1 consisting of the amino acid sequence set forth in SEQ ID NO: 3, a heavy chain CDR2 consisting of the amino acid sequence set forth in SEQ ID NO: 4, and a heavy chain CDR3 consisting of the amino acid sequence set forth in SEQ ID NO: 5; and a light chain variable region comprising a light chain CDR1 consisting of the amino acid sequence set forth in SEQ ID NO: 6, a light chain CDR2 consisting of the amino acid sequence set forth in SEQ ID NO: 7, and a light chain CDR3 consisting of the amino acid sequence set forth in SEQ ID NO: 8.

(13) The anti-HSV gB monoclonal antibody or antigen-binding fragment thereof according to the above (12), comprising:

a heavy chain variable region comprising the amino acid sequence set forth in SEQ ID NO: 1 and a light chain variable region comprising the amino acid sequence set forth in SEQ ID NO: 2.

(14) A polynucleotide encoding the anti-HSV gB monoclonal antibody or antigen-binding fragment thereof according to any one of the above (11) to (13).

(15) An expression vector comprising the polynucleotide according to the above (14) and one or more regulatory sequences operably linked to the polynucleotide.

Advantageous Effects of Invention

The anti-HSV gB monoclonal antibody or antigen-binding fragment thereof according to the present invention has strong virus-neutralizing activity (plaque number-reducing activity) to HSV-1 and HSV-2 in vitro, as well as strong cell to cell infection spread (intercellular transmission)-suppression activity, and the anti-HSV gB monoclonal antibody or antigen-binding fragment according to the present invention exhibits significant infection prevention effect not only after preventive administration, but also after therapeutic administration under the situation where HSV infection has been already established in the living body, also in vivo. Therefore, the anti-HSV gB monoclonal antibody or antigen-binding fragment thereof according to the present invention can be applied to the prevention and/or treatment and/or prevention of reactivation of HSV infection and can be used particularly as a preventive agent for immunocompromised patients having high risk of HSV infection or patients undergoing bone marrow transplantation, blood stem cell transplantation, or organ transplantation receiving an immunosuppressive agent, as a therapeutic agent for patients undergoing repetitive reactivation of HSV, or as an alternative drug or a concomitant drug of an existing antiviral drug.

BRIEF DESCRIPTION OF DRAWINGS

FIG. 13 is a figure illustrating the result of comparison by multiple alignment of an amino acid sequence (SEQ ID NO: 10) of gB derived from HSV-1 and an amino acid sequence (SEQ ID NO: 11) of gB derived from HSV-2, and the italic letters represent the leader sequence and the underlined letters represent amino acid residues 383-388 (I383-R388) in domain II of gB derived from HSV-1 and the amino acid residues 386-391 in domain II of gB derived from HSV-2.

DESCRIPTION OF EMBODIMENTS

Figure 1:
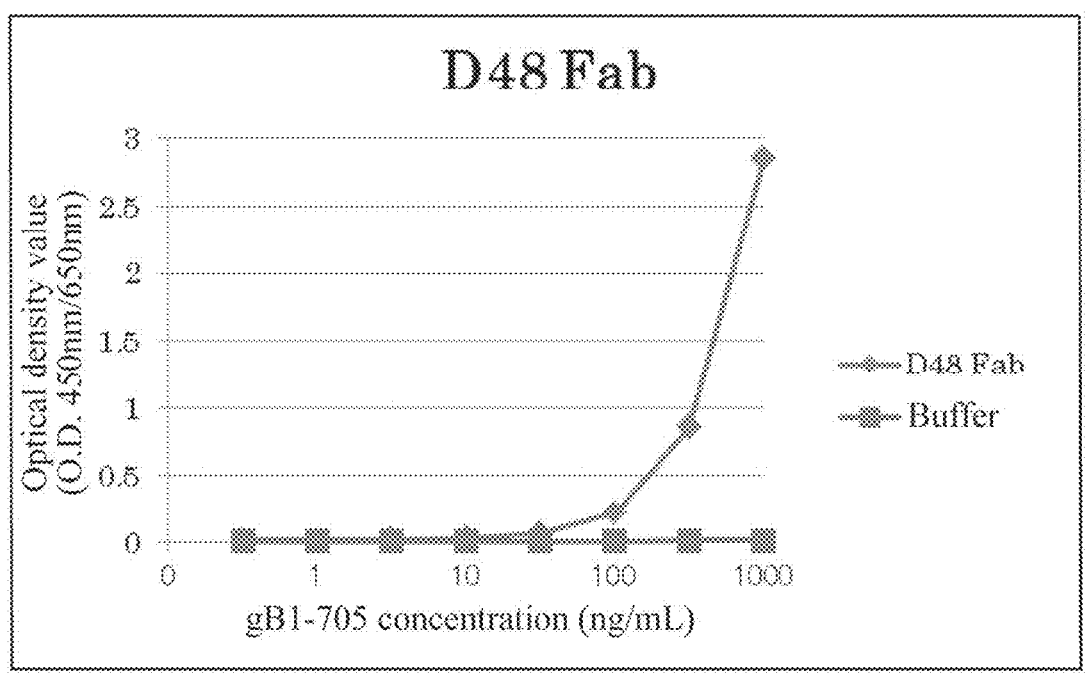
FIG. 1 is a figure illustrating the result of the reactivity analysis of an anti-HSV gB antibody (Fab) by the ELISA of Example 2.

Modes for carrying out the present invention will be described in detail below. The present invention is not limited to the following embodiments.

The anti-HSV gB monoclonal antibody or antigen-binding fragment thereof according to the present invention specifically binds to herpes simplex virus (HSV) envelope glycoprotein B (gB). The anti-HSV gB monoclonal antibody or antigen-binding fragment thereof according to the present invention comprises a heavy chain variable region comprising a heavy chain CDR1 consisting of the amino acid sequence set forth in SEQ ID NO: 3, a heavy chain CDR2 consisting of the amino acid sequence set forth in SEQ ID NO: 4, and a heavy chain CDR3 consisting of the amino acid sequence set forth in SEQ ID NO: 5, and a light chain variable region comprising a light chain CDR1 consisting of the amino acid sequence set forth in SEQ ID NO: 6, a light chain CDR2 consisting of the amino acid sequence set forth in SEQ ID NO: 7, and a light chain CDR3 consisting of the amino acid sequence set forth in SEQ ID NO: 8.

The present inventors obtained 44 anti-gB antibodies by comprehensive search of anti-HSV-2 gB antibodies conducted by using a human antibody library. As a result of examining those antibodies in a virus neutralization test, monoclonal antibody D48 exhibited strong plaque number-reducing activity and cell to cell infection spread-suppression activity.

Antibody D48 has a heavy chain variable region (VH) having the amino acid sequence set forth in SEQ ID NO: 1 and a light chain variable region (VL) having the amino acid sequence set forth in SEQ ID NO: 2 and a heavy chain variable region comprising a heavy chain CDR1, a heavy chain CDR2, and a heavy chain CDR3 consisting of the amino acid sequences set forth in SEQ ID NOs: 3-5 and a light chain variable region comprising a light chain CDR1, a light chain CDR2, and a light chain CDR3 consisting of amino acid sequences set forth in SEQ ID NOs: 6-8, shown in Table 1.

TABLE 1

VH and VL amino acid sequences of antibody D48 and CDRs thereof

| Region | | Amino acid sequence | SEQ ID NO. |
|---|---|---|---|
| VH | | EVQLVETGGGVVRPGRSLRLSCTTSGFSFSGSAMHWVRQAPG KGLEWVAVISHDGNIIQYHDSVKGRFTISRDNSKNVLLLQMNSLR VDDTAMYYCARDVWLLPATISYAFDFWGQGTMVTVSS | 1 |
| VL | | VIWMTQSPPSLSASIGDTVTITCRASQGISNSIAWYQRRPGKAPE LLVYAAYRLQSGVPSRLSGSGSGAEYTLTIKNMQPEDFATYYC QQYYDNPLTFGGGTKVEIK | 2 |
| VH | CDR1 | SGSAMH | 3 |
| | CDR2 | VISHDGNIIQYHDSVKG | 4 |
| | CDR3 | DVWLLPATISYAFDF | 5 |
| VL | CDR1 | RASQGISNSIA | 6 |
| | GDR2 | AAYRLQS | 7 |
| | CDR3 | QQYYDNPLT | 8 |

Since the anti-HSV gB monoclonal antibody or antigen-binding fragment thereof according to the present invention comprises CDR sequences of monoclonal antibody D48, it has strong virus-neutralizing activity (plaque number-reducing activity) to HSV-1 and HSV-2, as well as strong cell to cell infection spread (intercellular transmission)-suppression activity.

The anti-HSV gB monoclonal antibody or antigen-binding fragment thereof may comprise a heavy chain variable region comprising the amino acid sequence set forth in SEQ ID NO: 1 and a light chain variable region comprising the amino acid sequence set forth in SEQ ID NO: 2.

The anti-HSV gB monoclonal antibody is an antibody comprising at least a heavy chain variable domain and a light chain variable domain and may be a complete antibody. The complete antibody has 2 full length light chains and 2 full length heavy chains and the light chains and respective heavy chains are linked by disulfide bonds. The complete antibody includes IgA, IgD, IgE, IgM, and IgG, and IgG includes IgG$_1$, IgG$_2$, IgG$_3$, and IgG$_4$ as subtypes.

The antigen-binding fragment is also referred to as the antibody fragment and means a fragment with the function of binding to antigens (antigen-binding fragment). The antigen-binding fragment includes, for example, single chain variable region fragment (scFv), Fab, Fab', F(ab')$_2$, scAb, scFvFc, and Fv. Fab has one antigen-binding site as a structure having light chain and heavy chain variable regions and a light chain invariable region and the first heavy chain invariable region (CH1 domain). Fab' is different from Fab in that it has a hinge region containing at least a cysteine residue at the C terminus of the heavy chain CH1 domain. The F(ab')$_2$ antibody is produced by a disulfide bond between cysteine residues of the hinge region of Fab'. Fv (variable fragment) means the minimum antigen-binding fragment having only a heavy chain variable site and a light chain variable site. Double-stranded Fv (dsFv) has a heavy chain variable site linked with a light chain variable site by a disulfide bond and single chain Fv (scFv) has a heavy chain variable region linked with a light chain variable region by a covalent bond usually through a peptide linker. scAb is a fragment in which a partial domain (C domain) in an L-chain or H chain constant region is bound to scFv. scFvFc is a fragment in which CH1 and CH2 of the H chain are linked to scFv.

The antigen-binding fragment can be obtained, for example, from a complete antibody using a proteolytic enzyme. For example, the Fab fragment can be obtained by digesting a complete antibody with papain and the F(ab')$_2$ fragment can be obtained by digesting a complete antibody with pepsin. Moreover, the antigen-binding fragment can be produced using a gene recombination technique. The light chain and heavy chain variable regions contain 3 highly variable regions called complementarity-determining regions (hereinafter, referred to as "CDRs"). The CDRs mainly serve to bind to antigenic epitopes. The 3 CDRs are respectively called CDR1, CDR2, CDR3 in the order from the N-terminus.

The anti-HSV gB monoclonal antibody may be a human antibody (fully human antibody), a humanized antibody, or a chimeric antibody and is preferably a human monoclonal antibody or a humanized monoclonal antibody, in particular.

The anti-HSV gB monoclonal antibody or antigen-binding fragment thereof according to this embodiment specifically binds to herpes simplex virus (HSV) envelope glycoprotein B (gB). HSV gB includes gB derived from HSV-1 and gB derived from HSV-2 and FIG. 13 illustrates the result of comparison by multiple alignment of an amino acid sequence (SEQ ID NO: 10) of gB derived from HSV-1 and an amino acid sequence (SEQ ID NO: 11) of gB derived from HSV-2. According to FIG. 13, the identity between both sequences is 87%. The anti-HSV gB monoclonal antibody or antigen-binding fragment thereof according to this embodiment specifically binds to either of gB derived from HSV-1 and gB derived from HSV-2, particularly to domain II of gB and more particularly to I383-R388 of domain II of gB derived from HSV-1 or at least 1, at least 2, or furthermore at least 3 amino acid residues in the region corresponding to I386-R391 of domain II of gB derived from HSV-2.

The anti-HSV gB monoclonal antibody or antigen-binding fragment thereof according to this embodiment is considered to have the following 2 merits over existing antiviral drugs: (1) few side effects and (2) low risk of emergence of a resistant viral strain. As for the latter in particular, the emergence of HSV resistance that would be caused by a mutation in the epitope sequence in the gB protein is considered to be unlikely because the anti-HSV gB monoclonal antibody or antigen-binding fragment thereof according to this embodiment is an antibody that specifically binds to an epitope sequence on the HSV-1 and HSV-2 envelope surface glycoprotein B (gB) indispensable for the virus replication cycle and therefore it is considered that such a mutation itself should cause the loss of virus infectivity titer.

The anti-HSV gB monoclonal antibody or antigen-binding fragment thereof according to another embodiment of the present invention specifically binds to at least one amino acid residue in the region consisting of the amino acid residues 383-388 of the herpes simplex virus-1 (HSV-1) envelope glycoprotein B (gB) set forth in SEQ ID NO: 10, and/or at least one amino acid residue in the region consisting of the amino acid residues 386-391 of the herpes simplex virus-2 (HSV-2) envelope glycoprotein B (gB) set forth in SEQ ID NO: 11. Examples of the anti-HSV gB monoclonal antibody or an antigen-binding fragment thereof include those comprising a heavy chain variable region comprising a heavy chain CDR1 consisting of the amino acid sequence set forth in SEQ ID NO: 3, a heavy chain CDR2 consisting of the amino acid sequence set forth in SEQ ID NO: 4, and a heavy chain CDR3 consisting of the amino acid sequence set forth in SEQ ID NO: 5, and a light chain variable region comprising a light chain CDR1 consisting of the amino acid sequence set forth in SEQ ID NO: 6, a light chain CDR2 consisting of the amino acid sequence set forth in SEQ ID NO: 7, and a light chain CDR3 consisting of the amino acid sequence set forth in SEQ ID NO: 8.

As other embodiments, a polynucleotide encoding the monoclonal antibody or antigen-binding fragment thereof, an expression vector comprising the polynucleotide and one or more regulatory sequences operably linked to the polynucleotide, and a transformant comprising the expression vector are provided.

The polynucleotide may be a polynucleotide encoding a complete antibody and may be polynucleotides respectively encoding antigen-binding fragments comprising the amino acid sequences set forth in SEQ ID NOs: 1 to 8 and polynucleotides encoding a plurality of CDRs may be incorporated in one polynucleotide. Such a polynucleotide can be obtained, for example, by chemical synthesis.

The expression vector comprising a polynucleotide encoding an anti-HSV gB monoclonal antibody or an antigen-binding fragment thereof and one or more regulatory sequences operably linked to the polynucleotide according to this embodiment is not particularly limited, but may be a vector that can replicate and/or express a polynucleotide in host cells. Examples thereof include pCAG and pET. The regulatory sequence is a sequence that controls the expression of a polynucleotide in host cells (for example, a promoter, an enhancer, a ribosome-binding sequence, and a transcription termination sequence) and can be selected as appropriate depending on the kind of the host. The expression vector is operably linked to an appropriate promoter so that the polynucleotide can be expressed in host cells and may be a vector comprising a selection marker. Moreover, polynucleotides respectively encoding antigen-binding fragments comprising the amino acid sequences set forth in SEQ ID NOs: 1 to 8, for example, a polynucleotide encoding a heavy chain variable region and a polynucleotide encoding a light chain variable region may be expressed with separate vectors.

The host cells are not particularly limited as long as they are those that can express an antibody, but examples thereof include cells of a mammalian animal such as human, Chinese hamster, mouse, rat, rabbit, pig, monkey, goat, and horse, plant cells, yeast cells, insect cells, or bacterial cells. Methods for transforming the host cells are not particularly limited, but conventionally known methods such as electroporation, the calcium phosphate method, the liposome method, and the DEAE dextran method can be suitably used.

The monoclonal antibody or antigen-binding fragment thereof can be prepared, for example, by a known method of genetic engineering. The monoclonal antibody or antigen-binding fragment thereof can be prepared, for example, by expressing a vector comprising the polynucleotide encoding an anti-HSV gB monoclonal antibody or an antigen-binding fragment thereof in host cells. Those skilled in the art can appropriately design the polynucleotide depending on whether the antibody is a human antibody, a humanized antibody, or a chimeric antibody. For example, in the case of a human antibody or an antigen-binding fragment thereof, the polypeptide may further comprise in addition to the heavy chain and light chain variable regions set forth in SEQ ID NOs: 1 and 2 or polynucleotides encoding heavy chain CDR1-3 and light chain CDR1-3 set forth SEQ IDs NO: 3 to 8, at least a part of a polynucleotide encoding the amino acid sequence of the parts other than these parts of the human antibody. In the case of a complete antibody, such a polypeptide can be obtained by functionally linking a polynucleotide encoding the variable regions or CDR1-3 and a polynucleotide encoding the other parts in the right order. Polynucleotides encoding a heavy chain and a light chain may be incorporated in one polynucleotide or separate polynucleotides. Moreover, the polynucleotide may further comprise a polynucleotide(s) encoding a promoter for the expression and/or a tag necessary for confirmation of the expression. In the case of a chimeric antibody or an antigen-binding fragment thereof, the other parts other than the heavy chain and light chain variable regions set forth in SEQ ID NOs: 1 and 2 or the polynucleotides encoding heavy chain CDR1-3 and light chain CDR1-3 set forth SEQ IDs NO: 3 to 8 may comprise a polynucleotide encoding an amino acid sequence derived from an animal such as mouse or guinea pig.

A further embodiment provides a pharmaceutical composition for preventing or treating HSV infection, comprising an anti-HSV gB monoclonal antibody or an antigen-binding fragment thereof. The HSV infection comprises infection with HSV-1 and HSV-2 and examples thereof include herpes labialis, herpetic keratitis, genital herpes, systemic neonatal herpes, and stomatitis, dermatosis, encephalitis, meningitis, and myelitis caused by HSV.

The prevention means suppressing or delaying the onset of the infection or palliating symptoms by administration to a subject with risk of HSV infection, particularly an immunocompromised patient with high risk of HSV infection or a bone marrow transplantation, blood stem cell transplantation, or organ transplantation patient given an immunosuppressive agent. The treatment means palliation, improvement, or complete remission of symptoms by administration to a subject having already established HSV infection in the living body and includes the prevention of recurrence by administration to a subject undergoing repetitive HSV recurrence. The pharmaceutical composition for treating HSV infection may be used as an alternative drug or a concomitant drug of existing antiviral drugs.

The pharmaceutical composition may further comprise a pharmaceutically acceptable carrier. The pharmaceutically acceptable carrier is not particularly limited, but examples thereof include water, salt solutions, phosphate buffered physiological saline, dextrose, glycerol, ethanol, and the like. One of these carriers may be used alone or of two or more thereof may be used in a combination.

The pharmaceutical composition may be formulated into tablets, granules, capsules, an injection, an instillation, an inhaler, or a poultice. As a formulation agent for the purpose, the pharmaceutical composition may further comprise a small amount of an auxiliary substance that improves preservation or efficacy of an antibody or an antibody portion, for example, a lubricant, an emulsifier, an antiseptic, a buffer, an stabilizing agent.

EXAMPLES

The present invention will be described more specifically with reference to Examples below. However, the present invention is not limited to the following examples.

Example 1: Preparation of Anti-HSV gB Monoclonal Antibody D48

4 molecular forms, the scFv-hFc form, the Fab form, the human-murine chimeric IgG2a form, and the human-guinea pig chimeric IgG2κ form of antibody D48, which was obtained by comprehensive search of anti-HSV-2 gB (HSV gB2) antibodies conducted by using a human antibody library were prepared and further analyzed.

scFv-hFc

The isolated antibody D48 scFv (single chain Fv) gene encoding the amino acid sequence set forth in SEQ ID NO: 9 was linked to an Fc gene (CH2-CH3) derived from human IgG1 and cloned into the pCAG vector to construct an scFv-Fc expression plasmid. For expression, FreeStyle293 or Expi293 expression system (Life Technology Inc.) was used. Cells were transfected with the expression plasmid and culture supernatant was collected in 4 to 6 days. The culture supernatant was purified using Ab-Rapid PuRe 10 (ProteNova) or Ab-Rapid PuRe Ex (ProteNova) to obtain an scFv-hFc.

Fab

The VH region of the isolated antibody D48 scFv gene was linked to a CH1 gene derived from murine IgG2a and cloned into the pCAG vector to construct an H chain expression plasmid. Moreover, the VL region of the antibody D48 scFv gene was linked to a murine CL gene and cloned into the pCAG vector to construct an L chain expression plasmid. To facilitate purification, His tag gene was linked after (on the C terminal side of) the CH1 gene. For expression, FreeStyle293 or Expi293 expression system was used. Cells were transfected with the expression plasmid and culture supernatant was collected in 4 to 6 days. The culture supernatant was purified using Ni NTA Agarose (QIAGEN) to obtain a Fab.

Human-Murine Chimeric IgG2a

The VH region of the isolated antibody D48 scFv gene was linked to an H chain constant region gene (CH1-CH2-CH3) derived from murine IgG2a and cloned into the pCAG vector to construct an H chain expression plasmid. Moreover, the VL region of the antibody D48 scFv gene was linked to a murine CL gene and cloned into the pCAG vector to construct an L chain expression plasmid. For expression, FreeStyle293 or Expi293 expression system was used. Cells were transfected with the expression plasmid and culture supernatant was collected in 4 to 6 days. Culture supernatant was purified using a Hi Trap ProteinA HP Column (GE Healthcare) to obtain a human-murine chimeric IgG2a.

Human-Guinea Pig Chimeric IgG2κ

The VH region of the isolated antibody D48 scFv gene was linked to an H chain constant region gene (CH1-CH2-CH3) derived from guinea pig IgG2a and cloned into the pCAG vector to construct an H chain expression plasmid. Moreover, the VL region of the antibody D48 scFv gene was linked to a murine CL gene and cloned into the pCAG vector to construct an L chain expression plasmid. For expression, FreeStyle293 or Expi293 expression system was used. Cells were transfected with the expression plasmid and culture supernatant was collected in 4 to 6 days. Culture supernatant was purified using a Hi Trap ProteinA HP Column to obtain a human-guinea pig chimeric IgG2κ.

Example 2 Reactivity Analysis of Anti-HSV gB Antibody by ELISA

Reactivity Analysis of Fab

The binding activity of the obtained Fab was evaluated by ELISA. The Fab was diluted to 2 µg/mL in PBS and immobilized by transferring 100 µL into a MaxiSorp plate (Nunc) and incubating the plate at room temperature for 2 hours. After the immobilization, the plate was washed with PBS and 100 µL solutions of a recombination HSV-1 gB (gB1-705-strep) serially diluted 3.16-fold each from 1 µg/mL to 0.316 ng/ml were added to wells of the plate, which was incubated at 37° C. One hour later, the plate was washed with PBST and 100 µL aliquots of the detection antibody anti-strep-Tactin/HRP (Funakoshi) were added to the wells of the plate, which was incubated at 37° C. One hour later, the plate was washed with PBST and 100 µL of TMB (3,3',5,5'-tetramethylbenzidine) was added to each well of the plate for the color development. 30 minutes later, the reaction was stopped with 1 N sulfuric acid and the color value (O. D. 450 nm/650 nm) was measured with a microplate reader (Molecular Devices). The recombinant gB (gB1-705-strep) used was one obtained by connecting Strep tagII to the C terminus of the ectodomain of the wild type gB, derived from HSV-2 strain 333, consisting of 1st to 705th amino acid residues of the amino acid sequence set forth in SEQ ID NO: 11 and the purification and the detection by ELISA were conducted using this tag.

As a result, the recombination gB (gB1-705-strep) exhibited specific binding to the antibody D48 Fab, as shown in FIG. 1.

Reactivity Analysis of Human-Murine Chimeric IgG2a

The binding activity of the obtained human-murine chimeric IgG2a was evaluated by ELISA. A recombinant gB (gB1-705-strep) was diluted to 1 µg/mL with PBS and 100 µL was transferred into a MaxiSorp plate and the recombinant gB (gB1-705-strep) was immobilized by incubating the plate at room temperature for 1 hour. After the immobilization, the plate was washed with PBS and 100 µL solutions of the human-murine chimeric IgG2a serially diluted 3.16-fold each from 1 µL to 0.316 ng/ml were added to wells of the plate, which was incubated at 37° C. One hour later, the plate was washed with PBST and 100 µL solutions of the detection antibody rabbit anti-mouse IgG/HRP (invitrogen) was added to the wells of the plate, which was incubated at 37° C. One hour later, the plate was washed with PBST and 100 μL of TMB was added to each well of the plate for the color development. 30 minutes later, the reaction was stopped with 1 N sulfuric acid and the color value (O.D. 450 nm/650 nm) was measured with a microplate reader.

Figure 2:
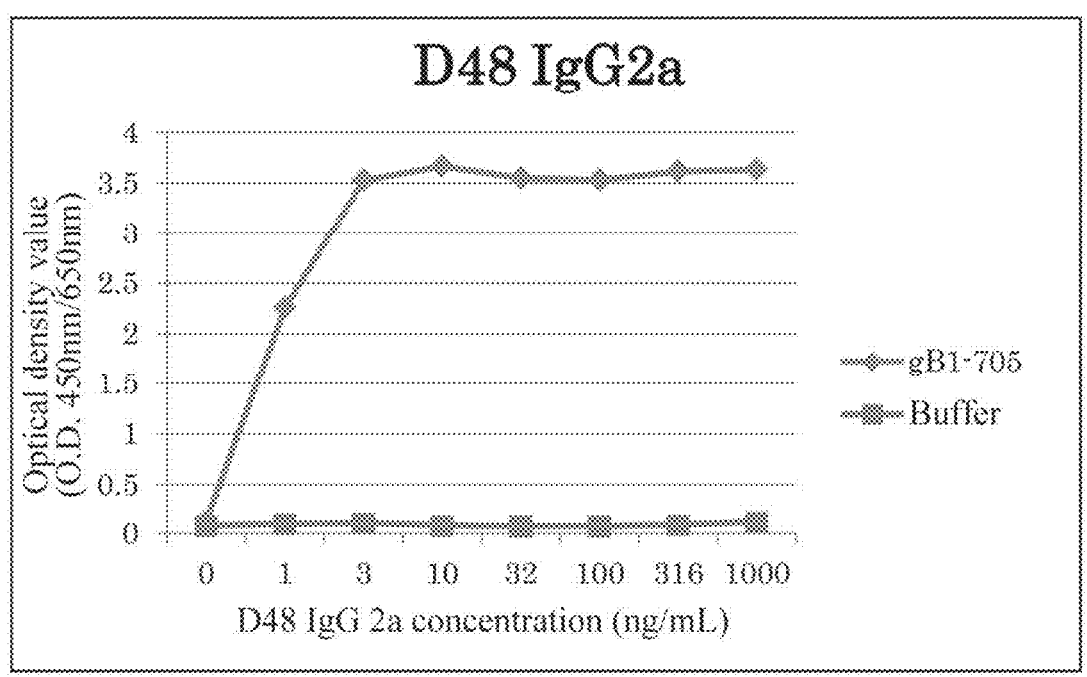
FIG. 2 is a figure illustrating the result of the reactivity analysis of an anti-HSV gB antibody (human-murine chimeric IgG2a) by the ELISA of Example 2.

As a result, the human-murine chimeric IgG2a exhibited specific binding to the recombinant gB (gB1-705-strep), as illustrated in FIG. 2.

Example 3 Reactivity Analysis of Anti-HSV gB Antibody by Immunoblotting

2 μg/lane of gB1-705-strep was loaded in an 8-16% by weight SDS-PAGE gel and electrophoresis was performed. After the electrophoresis, transfer from the gel to a nitrocellulose membrane (Immobilon-P, MILLIPORE) was made and the membrane was blocked with 2% skim milk (Wako)-PBST. The nitrocellulose membrane blocked was washed with PBST and incubated with 2% skim milk-PBST and 10 μg/mL of scFv-hFc, Fab, human-murine chimeric IgG2a or human-guinea pig chimeric IgG2κ at room temperature for 60 minutes. After washing again, the nitrocellulose membrane was incubated with anti-hIgG (H+L)/HRP (BIO-RAD), anti-His tag/HRP (R & D), anti-mouse IgG (H+L)/HRP, or anti-guinea pig (H+L)/HRP (Invitrogen) in 2% skim milk-PBST and developed in Immobilon Western Detection Regent (Millipore). Native gB1-705-strep, denatured gB1-705-strep and reduced and denatured gB1-705-strep were prepared. The reduced and denatured gB1-705-strep was obtained by adding 1 M DTT and boiling the mixture at 96° C. for 5 minutes. The denatured gB1-705-strep was obtained by boiling gB1-705-strep at 96° C. for 5 minutes. The native gB1-705-strep is gB1-705-strep without these treatments. The prepared native gB1-705-strep, denatured gB1-705-strep, and reduced and denatured gB1-705-strep were directly loaded into a gel.

Figure 3:
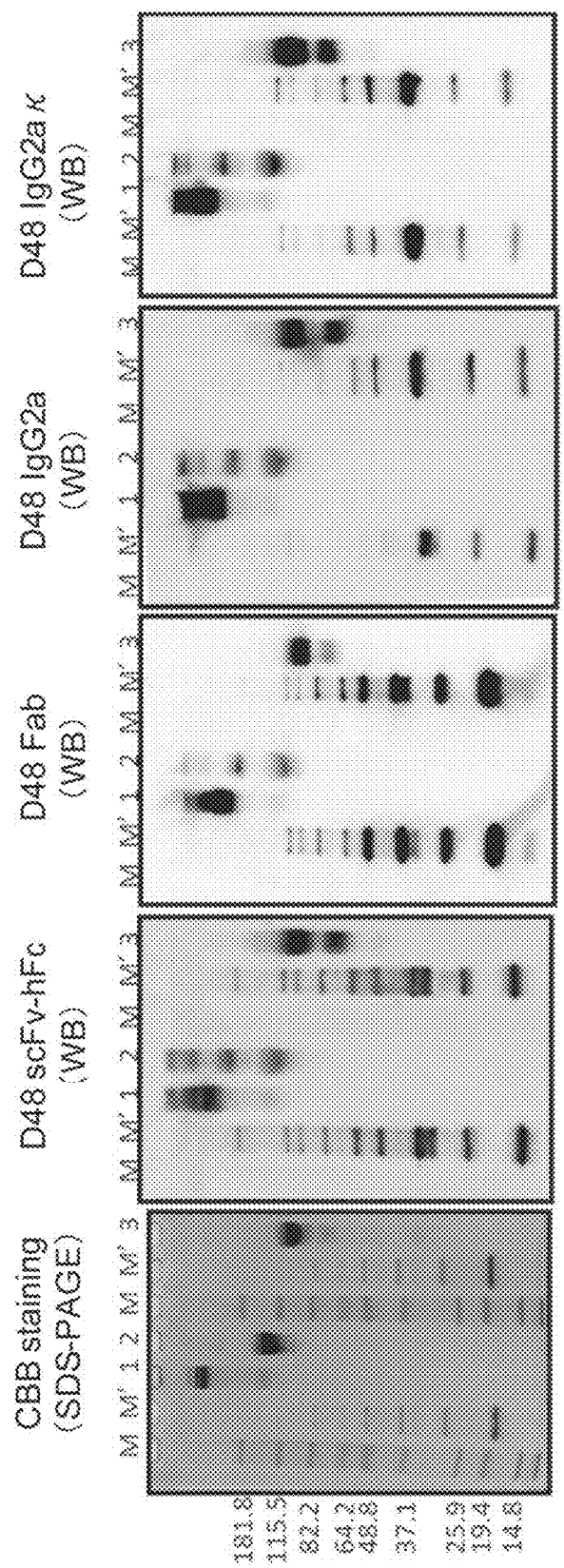
FIG. 3 is a figure illustrating the result of the reactivity analysis of anti-HSV gB antibodies by immunoblotting of Example 3.

The results are shown in FIG. 3. Lanes 1 to 3 were native gB1-705-strep, denatured gB1-705-strep, and reduced and denatured gB1-705-strep, in order, and Lanes M and M' were respectively BenchMark prestained Ladder and Magic Western standard. The left photograph is of SDS-PAGE and CBB staining was performed for the band staining The 4 right photographs were the results of Western blotting (WB). As seen in FIG. 3, the original scFv-hFc had an interesting characteristic to strongly react to reduced and denatured gB1-705-strep in comparison with native gB1-705-strep and this characteristic was shared to the Fab form, the human-murine chimeric IgG2a form, and the human-guinea pig chimeric IgG2κ form, which are the modified molecule forms. It is considered that antibodies that strongly react to denatured antigen epitopes are likely to recognize linear sequences. Accordingly, it is speculated that antibody D48 recognizes a linear sequence of gB from this result.

Example 4 Analysis by Surface Plasmon Resonance (SPR)

The analysis was performed using Biacore T200 (GE Healthcare). In all experiments, HBS-EP+buffer was used and the temperature was set at 25° C. and the flow rate was set to 30 μL/m. The sensor tip used was CM5 (GE Healthcare) and about 100 resonance units (RU) of gB1-705-strep was immobilized. The measurement is conducted in the single cycle kinetics mode. scFv-hFc was used at 128 nM, 64 nM, 32 nM, 16 nM, 8 nM; Fab was used at 64 nM, 32 nM, 16 nM, 8 nM, 4 nM; and human-murine chimeric IgG2a, human-guinea pig chimeric IgG2κ, monoclonal antibody E31, and monoclonal antibody F67 were used at 256 fold, 128 fold, 64 fold, 32 fold, and 16 fold dilutions. All samples were measured only once. Monoclonal antibody E31 and monoclonal antibody F67 are both antibodies that recognizes domain IV of gB.

The result is shown in Table 2. Also from the kinetic analysis using SPR, it was suggested that the affinity was maintained. Also from the kinetic analysis, it was found that F67 and E31, which are other antibody strains obtained by comprehensive search of anti-HSV HSV gB2 antibodies using a human antibody library, have affinities that are 1 order lower than that of antibody D48.

TABLE 2

Results of kinetic analysis of various molecular forms of antibody D48

| Clone | Molecular form | $K_D$ (M) |
|---|---|---|
| D48 | scFv-hFc | $8.1 \times 10^{10}$ |
| D48 | Fab | $5.8 \times 10^{10}$ |
| D48 | IgG2a | $7.4 \times 10^{10}$ |
| D48 | IgG2a | $7.6 \times 10^{10}$ |
| E31 | IgG2a | $4.5 \times 10^{9}$ |
| F67 | IgG2a | $3.0 \times 10^{9}$ |

Example 5 Epitope Analysis by Alanine Scanning

To identify the epitope of antibody D48, 187 clones in which a charged amino acid contained in gB1-705 is substituted by alanine were prepared and the reactivity to the scFv-hFc of antibody D48 was examined.

The genes in which the charged amino acid residues (187 positions) in gB1-705 were changed to alanine were constructed by PCR and cloned into pCAGGS1-dhfr-neo. For expression, FreeStyle293 or Expi293 expression system was used. The expression levels of the obtained gB alanine substitutes and the binding activity of alanine substitutes to the antibody fragment was evaluated by ELISA.

Culture supernatants containing the gB alanine substitutes were transferred to a MaxiSorp plate and the gB alanine substitutes were immobilized by incubating the plate at room temperature for 1 hour. After the immobilization, the plate was washed with PBST and 100 μL solutions of the detection antibody StrepTactin/HRP (IBA) were added to the wells of the plate, which was incubated at room temperature. One hour later, the plate was washed with PBST and 100 μL solutions of TMB were added to the wells of the plate for the color development. 30 minutes later, the reaction was stopped with 1 N sulfuric acid and the color values (O.D. 450 nm/650 nm) were measured with a microplate reader to determine the expression levels.

Meanwhile, the culture supernatants containing the gB alanine substitutes were transferred into a MaxiSorp plate on which Streptactin (IBA) was immobilized and the gB alanine substitutes were immobilized by incubating the plate at room temperature for 1 hour. After the immobilization, the plate was washed with PBST and 100 μL solutions of the antibody fragment were added to the wells of the plate, which was incubated at room temperature. One hour later, the plate was washed with PBST and 100 μL solutions of the detection antibody anti-human Fc/HRP (Cosmo bio) were added into the wells of the plate, which was incubated at room temperature. One hour later, the plate was washed with PBST and 100 μL solutions of TMB were added to the wells of the plate for the color development. 30 minutes later, the reaction was stopped with 1 N sulfuric acid and the color values (O.D. 450 nm/650 nm) were measured with a microplate reader to determine the binding activity. Epitope candidates were selected on the basis of whether the reactivity per expression level is changed in comparison with that of the wild type gB1-705 with no alanine substitution.

As a result, it has been suggested that R391 on domain II of gB is an amino acid residue that is important as an epitope.

Example 6 Epitope Analysis by Hydrogen-Deuterium Exchange Mass Spectrometry (HDX-MS)

Alanine scanning is an analysis that targets only hydrophilic residues and the possibility that other non-hydrophilic residues may be epitopes was well expected.

Therefore, a detailed epitope analysis of antibody D48 was conducted using hydrogen-deuterium exchange mass spectrometry (HDX-MS). This technique takes advantage of the phenomenon in which amide hydrogen (H) not forming a stable hydrogen bond on the surface of the structure and in intrinsically disordered regions is rapidly exchanged for D when the protein is exposed to $D_2O$. For example, the antibody-protein interface where an antibody has formed tight binding would be strongly protected from HDX since the entry of $D_2O$ is allowed only by breathing motion and, as a result, only low rate HDX occurs. Meanwhile, since places other than the antibody-protein interface are not protected from HDX, high rate HDX occurs, as a result. By analyzing the mass change of the antibody-protein complex having undergone HDX heterogeneously due to this difference of the HDX rate by MS-based peptide mapping, detailed epitope analysis of the antibody is possible. HDX-MS has already become an established technique with applied results in many fields and, particularly in the epitope analysis of antibodies, it has become an important technique in that it allows analysis of conformational epitopes with maintaining the conformation in solution.

The procedure of the experiment was as follows. 120 µM gB1-705 and 400 µM antibody D48 Fab that are the same amount were mixed to prepare a gB1-705/antibody D48 Fab complex. This complex was prepared in PBS (pH 7.2) and H/D exchange reaction was performed at 20° C. using PBS (pD7.2) as a deuterium buffer. To the complex after the reaction were added Quench buffer (100 mM sodium phosphate, 150 mM sodium chloride, 4M guanidine hydrochloride, 150 mM tris(2-carboxyethyl)phosphine hydrochloride (TCEP)) and a mixture was prepared to be pH 2.4. Using a pepsin column, the complex was processed into peptide fragments, which were analyzed by LC-MS. Digestion and elution conditions in this process were Injected sample: 75 pmol, time for pepsin digestion+desalination: 6 minutes, gradient condition for LC: 9 minutes. 192 peptides were common to three times of measurement of gB1-705, gB1-705/antibody D48 Fab complex under such conditions and the sequence coverage was 99.2%.

Figure 4:
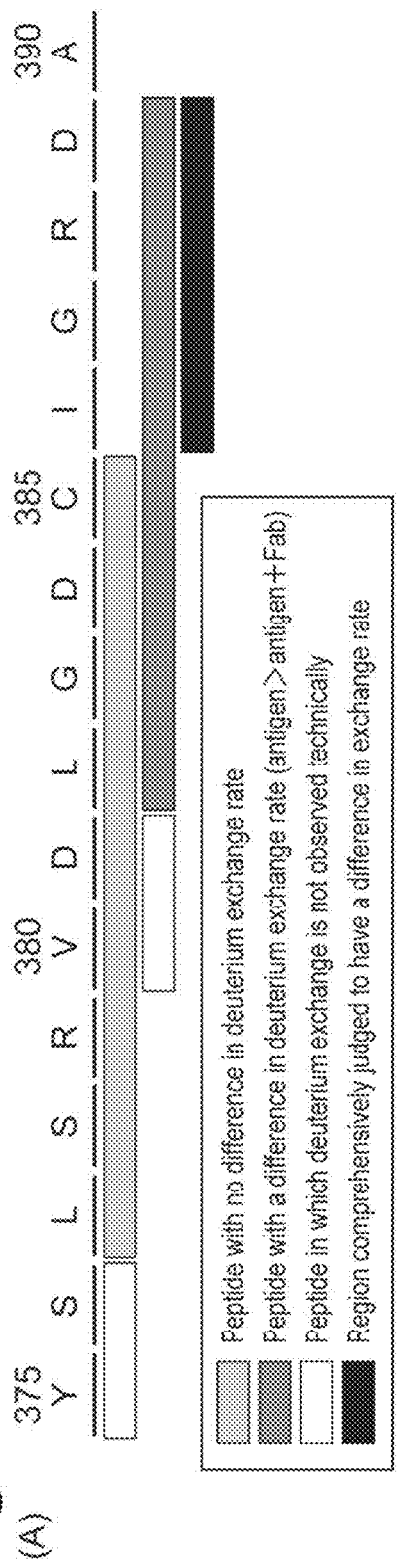
FIG. 4 is a figure illustrating the result of the epitope analysis by the hydrogen-deuterium exchange mass spectrometry (HDX-MS) of Example 6. The sequence shown in this figure, "YSLSRVDLGDCIGRDA" corresponds to amino acids 375-390 of SEQ ID NO:11.
Figure 4:
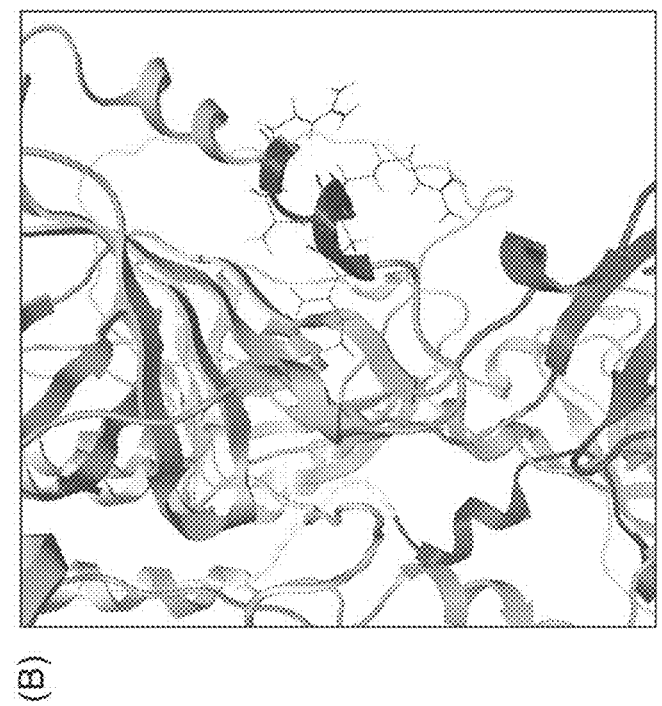

The result of the epitope analysis by the hydrogen-deuterium exchange mass spectrometry (HDX-MS) is shown in FIG. 4. As a result of analysis using gB1-705 and antibody D48 Fab, the peptide V380-D389 made a hit. Moreover, since L377-C385 was judged to be a peptide with no difference in the deuterium exchange rate, I386-D389 was suggested to be an epitope of antibody D48. This is very close to R391, the result of the previous analysis by the present inventors.

Moreover, pepsin is used as a digestive enzyme in this study and it was not possible to obtain any peptide containing R391, but, taken together, the possibility that I386-R391 in HSV-2 gB set forth in SEQ ID NO: 11 is an epitope of antibody D48 is considered to be very high. Moreover, it is considered that there is a possibility that either one of D389, R388, G387, and I386 is the epitope. Furthermore, it is also possible that a part of the epitope is composed of a residue after R391. Similarly, the possibility that the region consisting of I383-R388 of HSV-1 set forth in SEQ ID NO: 10 corresponding to I386-R391 of HSV-2 gB set forth in SEQ ID NO: 11 is an epitope of antibody D48 is considered to be very high.

Referring to the conformation, I386-R391 forms an alpha helix located in the protein-solvent interface of gB domain II and is considered to be a site easily accessible to antibodies. Moreover, L416-L422 did not satisfy the criteria for hit, but a difference in the deuterium exchange rate was detected. Since L416-L422 is located more inside in the structure than I386-R391 and resides at the position that is unlikely to be exposed to solvent, this difference in deuterium exchange rate is considered to reflect the effect of structural change.

While C226, H1838, and H1781, of already reported antibodies, are known as anti-HSV gB monoclonal antibodies to recognize epitopes on domain II of HSV gB and approximate epitopes and in vitro bioactivity have been reported, there is no report on details of in vivo bioactivity (Non-Patent Literature 18).

Example 7: Virus Neutralization Test

Culture of Cells and Viruses

For culture of viruses, measurement of infectivity titer, and measurement of neutralizing antibody titer, Vero cells (CCL.81) purchased from ATCC were used. The Vero cells were cultured under conditions at 37° C. and 5% $CO_2$. A MEM medium supplemented with 10% FBS was used at the time of preparing plates for expansion, maintenance, and analysis and an MEM medium supplemented with 2% FBS was used at the time of the measurement of infectivity titer and the measurement of neutralizing antibody titer. For the virus bank used in the neutralization test and the analysis of protective ability against infection, human herpesvirus 2 (HSV-2) strain MS (VR-540) and human herpesvirus 1 (HSV-1) strain KOS (VR-1493) purchased from ATCC was inoculated onto full sheets of Vero cells at a m.o.i=0.01 to 1 and cultured in the MEM medium supplemented with 2% FBS for 2 to 3 days. Collected culture bottles of the infected cells were freeze-thawed three times; to disrupt the cells and then centrifuged at room temperature in a TOMY centrifuge at 3500 rpm for 10 minutes to obtain supernatant as the HSV-2 virus bank and the HSV-1 virus bank.

Neutralization Test

The neutralization test was conducted using 2 methods: the measurement of plaque number-reducing activity (plaque reduction activity) and the measurement of cell to cell infection spread-suppression activity. The viruses used in the test were 2 viruses: HSV-2 strain MS and HSV-1 strain KOS.

For the measurement of plaque reduction activity, a test antibody is prepared at a predetermined concentration and mixed with about 100 PFU of HSV-2 strain MS or HSV-1 strain KOS and then incubated at 37° C. for 1 hour. The resultant reaction solution was seeded onto Vero cells allowed to become full sheets in a 48-well plate, left for the adsorption at 30° C. for 1 hour, and then cultured in a MEM (2% FBS) medium supplemented with 1% methylcellulose for 24 hours, and then the inactivation and the fixation were performed with 50% methanol/50% ethanol (−20° C.) at −20° C. for 30 minutes. Subsequently, this was incubated with the anti-HSV gB monoclonal antibody at 37° C. for 1 hour and immunostained with an anti-mouse IgG/HRP (Dako P0447) and TMBH and images of the respective wells were taken in an ELISPOT analyzer (ImmunoSpot S6 Analyzer CTL) to count the number of plaques using an analysis soft (BioSpot CTL).

For the measurement of cell to cell infection spread-suppression activity, about 100 PFU of HSV-2 strain MS or HSV-1 strain KOS was inoculated onto Vero cells allowed to become full sheets in a 48-well plate and left for the adsorption at 30° C. for 1 hour, and then a MEM (2% FBS) medium supplemented with 1% methylcellulose containing a test antibody at a predetermined concentration (the antibody concentrations are 5, 25 and 125 μg/mL) was added; and HSV-2 strain MS was cultured for about 40 hours and HSV-1 strain KOS was cultured for 48 hours and then the inactivation and the fixation were performed with 50% methanol/50% ethanol (−20° C.) at −20° C. for 30 minutes. Subsequently, they were incubated with an anti-HSV gB monoclonal antibody prepared in house at 37° C. for 1 hour and immunostained with an anti-mouse IgG/HRP and TMBH and images of the respective wells were taken in an ELISPOT analyzer to analyze the average of the plaque size using an analysis software.

The results are shown in Table 3. Any of scFv-hFc, Fab, human-murine chimeric IgG2a, and human-guinea pig chimeric IgG2k of antibody D48 exhibited a strong 50% plaque number-reducing activity of 1 nM or less or several nM to both strains KOS (HSV-1) and MS (HSV-2). Moreover, scFv-hFc and human-murine chimeric IgG2a of antibody D48 exhibited strong 50% cell to cell infection spread-suppression activities of 40 nM and 48 nM respectively to the strain MS (HSV-2).

TABLE 3

Neutralizing activity of various molecular forms of antibody D48

| Molecular form of antibody D48 | 50% plaque number-reducing activity | | 50% cell-to-cell infection spread-suppression activity | |
|---|---|---|---|---|
| | Strain KOS (HSV-1) [nM] | Strain MS (HSV-2) [nM] | Strain KOS (HSV-1) [nM] | Strain MS (HSV-2) [nM] |
| scFv-hFc | 1 | 0.12 | N.T. | 40 |
| Fab | 2.7 | 4.4 | N.T. | N.T. |
| IgG2a | 1.9 | 1.6 | N.T. | 48 |
| IgG2κ | 0.94 | 7.5 | N.T. | N.T. |

N.T.: not tested

50% plaque number-reducing activities of antibody D48 in vitro against HSV-1 and HSV-2 are outstanding in comparison with a variety of anti-HSV gB monoclonal antibodies previously reported.

Example 8 Murine Infection-Prevention Test

Method of Testing

Using a mouse model of genital herpes infection, an infection-prevention test upon preventive administration and therapeutic administration of an anti-HSV gB monoclonal antibody (human-murine chimeric IgG2a) was conducted. BALB/c mice (5 weeks old, female) were used. A predetermined amount of the antibody was dissolved in physiological saline for injection and the antibody was administered to the mice. For preventive administration, the antibody in a volume of 200 μL/animal was intraperitoneally administered 24 hours before the inoculation of virus. For therapeutic administration, the antibody in a volume of 200 μL/animal was intraperitoneally administered 48 hours before the inoculation of virus. The number of animals was set at N=10 per group. To improve multiplicity of infection upon the inoculation of virus, 2 mg/animal of Depo-Provera was inoculated subcutaneously 6 days before the inoculation of virus. $5 \times 10^5$ PFU/20 μL of HSV-2 strain MS was transvaginally inoculated under anesthesia and follow-up was conducted for 21 days. Infection prevention ability was expressed by survival time (survival rate) and symptom score as indicators. The symptom score was defined by the presence or absence and degree of vaginal lesion symptoms and expressed as the mean of each group. The scores were defined as follows: 0: no change, 1: partial erythema/swelling, 2: extensive swelling/edema, 3: ulcer/hemorrhage, 4: death. When serious general symptoms (piloerection, paralysis, tremor, convulsion, and the like) with no possibility of recovery are observed, the animal was given a score of 3.5 on the day of observation and sacrificed, and given a score of 4 next day, handled as dead.

Mouse Infection-Prevention Test with Antibodies D48, F67, and E31

The mouse infection prevention abilities of the 3 anti-HSV gB2 antibodies D48, F67, and E31 (all human-murine chimeric IgG2a) set forth in Table 4 were evaluated and compared. While antibody D48 is an antibody having an epitope in domain II region of HSV gB and having strong virus-neutralizing activity (50% plaque number-reducing activity), F67 and E31 both have an epitope in domain IV region and the former had no virus-neutralizing activity and the latter had intermediate virus-neutralizing activity.

TABLE 4

Neutralizing activity and epitope region of antibodies D48, F67, and E31

| Human-murine chimeric IgG2a | 50% plaque number-reducing activity [Strain MS] (nM) | Epitope region |
|---|---|---|
| D48 | 1.6 | Domain II Amino acid sequence containing I386-R391 |
| F67 | >5000 | Domain IV Reduction of binding ability by alanine substitution of any one of R613, E626, E627, and H632 |
| E31 | 67 | Domain IV Reduction of binding ability by alanine substitution of any one of D554, R563, and D583 |

Figure 5:
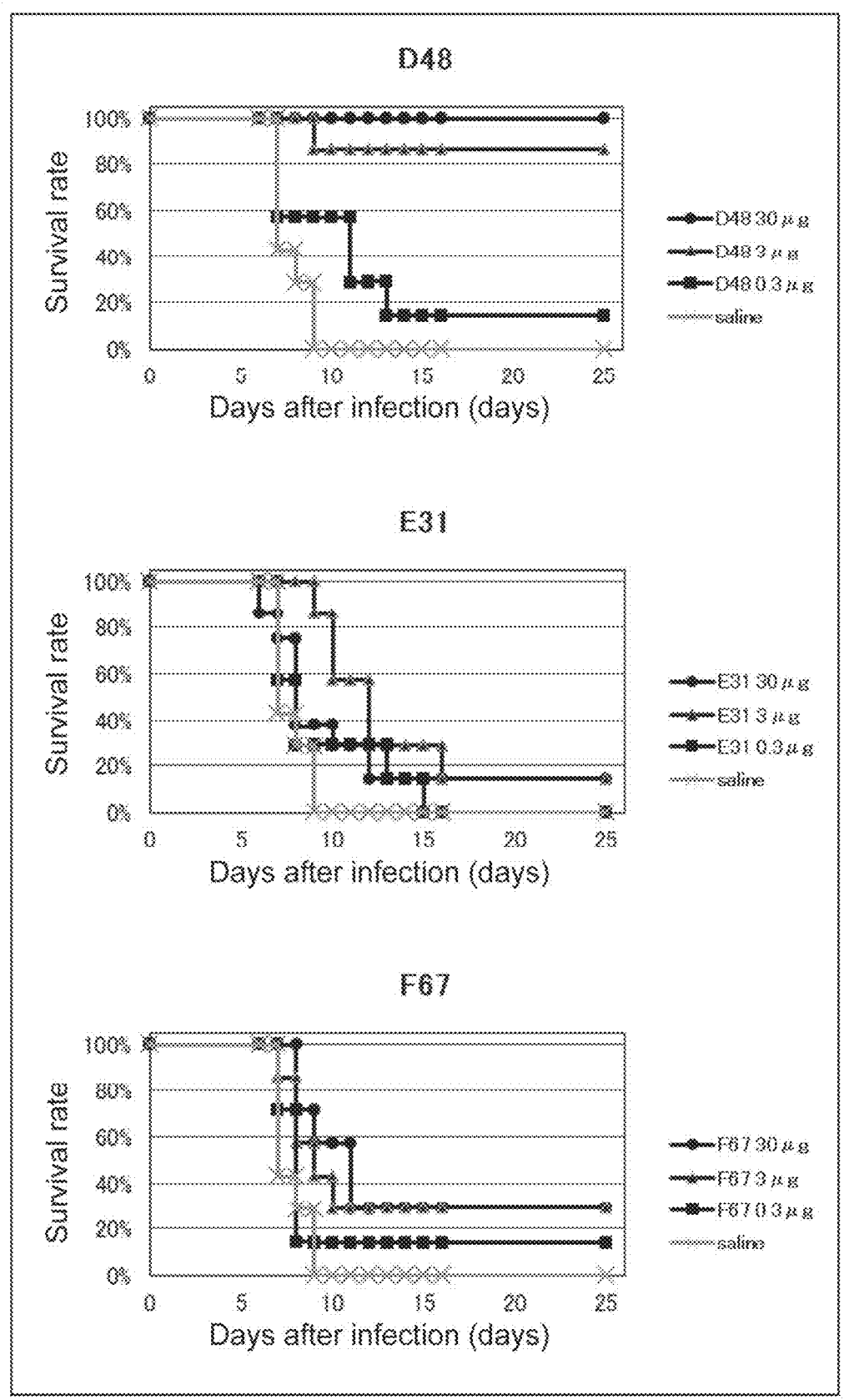
FIG. 5 is a figure illustrating the result of comparison of survival rates in a mouse infection-prevention test with antibodies D48, F67, and E31 of Example 8.

Preventive administration in which the number of animals per group was n=7 was performed. The survival time after the infection and the mean thereof are shown in Table 5 and the mean of survival rate (%) after the infection is shown in FIG. 5. As to the mouse infection prevention ability, while antibody D48 exhibited prominent survival time prolongation effect at 30 μg/animal/dose and 3 μg/animal/dose and significant survival time prolongation effect even at 0.3 μg/animal/dose, F67 and E31 both exhibited only limited effect. From this result, the possibility was suggested that antibody D48 has prominent infection prevention activity in comparison with other anti-HSV gB2 antibodies not only in vitro but also in vivo and the superiority is based on the difference of epitope region and affinity.

TABLE 5

Survival time after preventive administration of IgG2a of antibodies D48, F67, and E31 to mice

| Human-marine chimeric IgG2a | Inoculation amount (μg/animal/dose) | Survival time after infection (days) | Mean survival time (days) | Significant difference test (vs saline) |
|---|---|---|---|---|
| D48 | 30 | >28, >28, >28, >28, >28, >28 | >28 | *** |
|  | 3 | 8, >28, >28, >28, >28, >28, >28 | >28 | ** |
|  | 0.3 | 6, 6, 6, 10, 10, 12, >28 | 10 | * |
| F67 | 30 | 7, 7, 8, 10, 10, >28, >28 | 10 | * |
|  | 3 | 6, 7, 7, 8, 9, >28, >28 | 8 | N.S. |
|  | 0.3 | 6, 6, 7, 7, 7, 7, >28 | 7 | N.S. |
| E31 | 30 | 5, 6, 7, 7, 9, 11, >28 | 7 | N.S. |
|  | 3 | 8, 9, 9, 11, 11, 15, >28 | 11 | ** |
|  | 0.3 | 6, 6, 6, 7, 7, 12, 14 | 7 | N.S. |
| saline |  | 6, 6, 6, 6, 7, 8, 8 | 6 |  |

[Significant difference test] *: $p < 0.001$, : $0.001 \leq p < 0.01$, *: $0.01 \leq p < 0.05$ (Kaplan-Meier method)

Result of Mouse Infection-Prevention Test with Antibody D48

Figure 6:
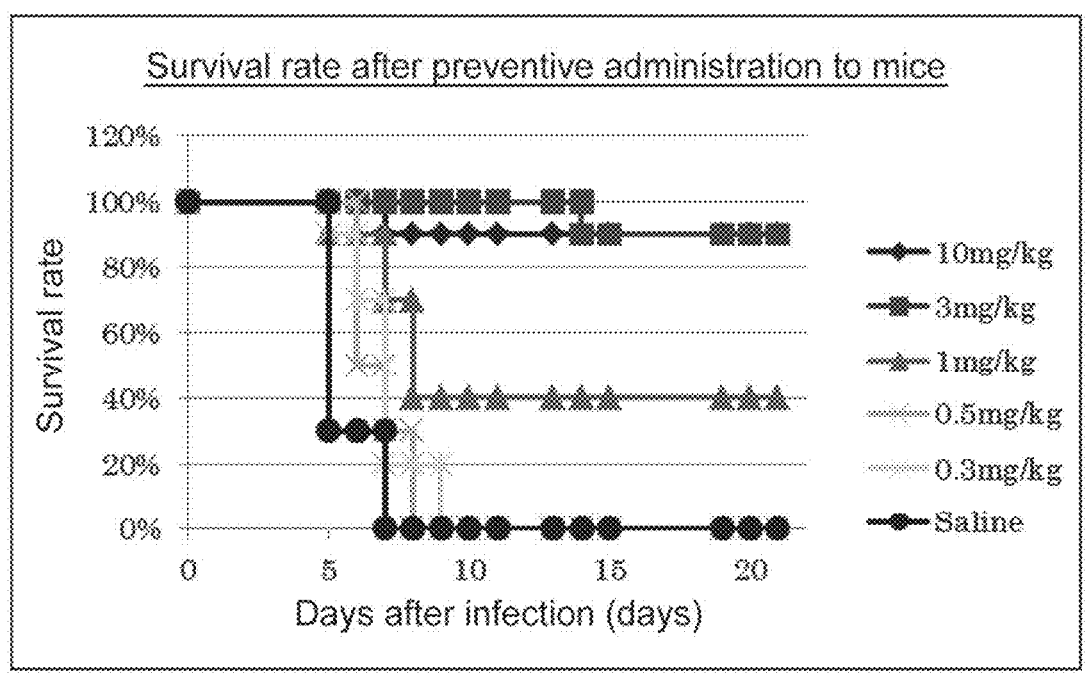
FIG. 6 is a figure illustrating the result of survival rates from the preventive administration to mice of antibody D48 of Example 8.
Figure 7:
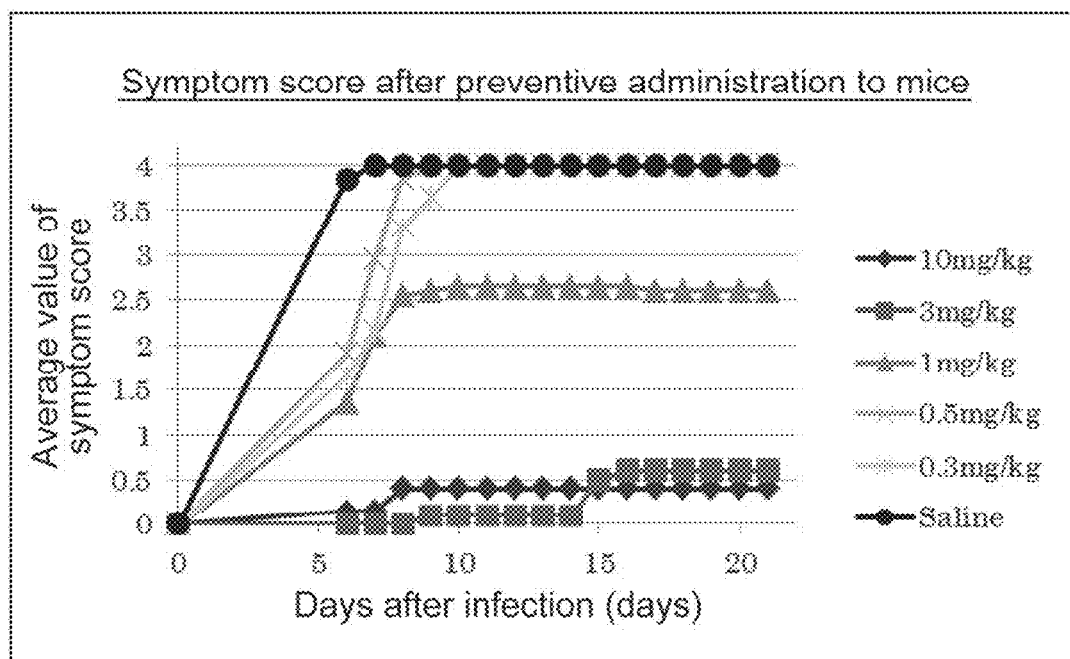
FIG. 7 is a figure illustrating the result of symptom scores after the preventive administration to mice of antibody D48 of Example 8.
Figure 8:
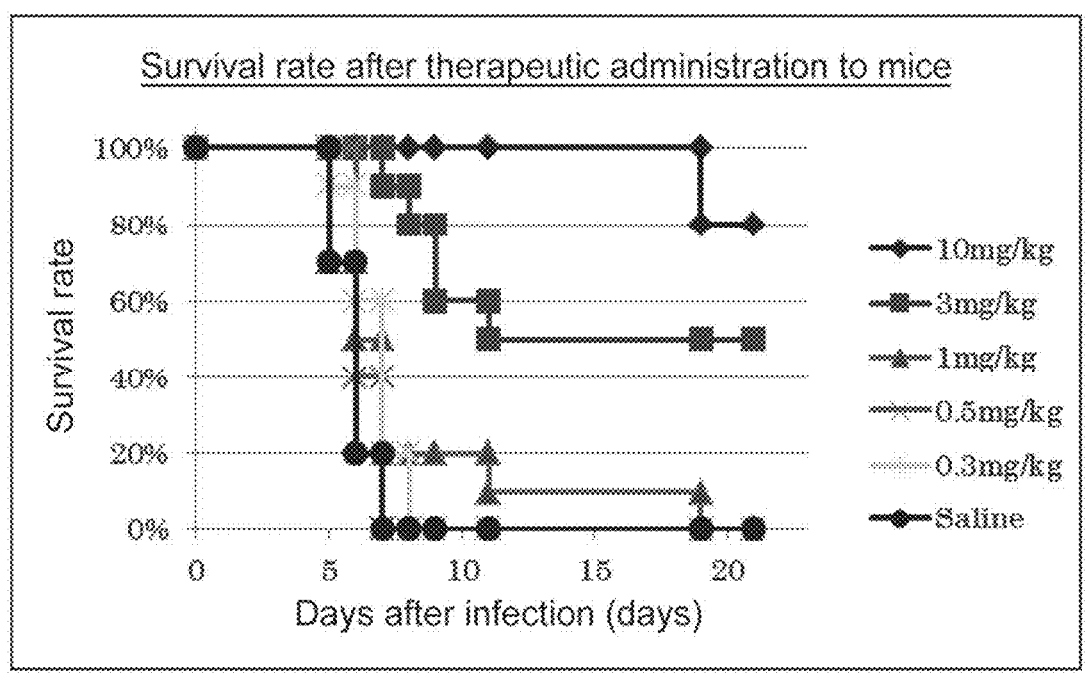
FIG. 8 is a figure illustrating the result of survival rates after the therapeutic administration to mice of antibody D48 of Example 8.
Figure 9:
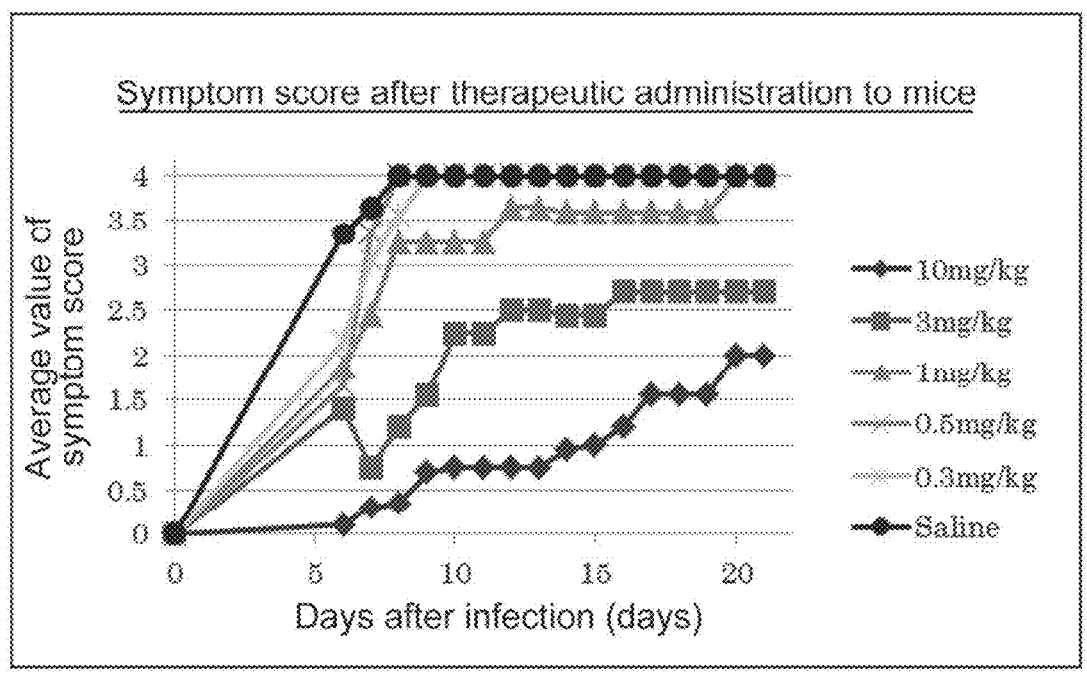
FIG. 9 is a figure illustrating the result of symptom scores after the therapeutic administration to mice of antibody D48 of Example 8.

The results of infection-prevention tests in preventive administration and therapeutic administration of antibody D48 (human-murine chimeric IgG2a) using a mouse model of genital herpes infection (n=10) are shown. The results of preventive administration are shown in Table 6 (survival time by dosage), FIG. 6 (survival rate), and FIG. 7 (symptom score). The results of therapeutic administration are shown in Table 7 (survival time by dosage), FIG. 8 (survival rate), and FIG. 9 (symptom score).

In the preventive administration, significant survival time prolongation effect was exhibited at all doses set (10 mg/kg, 3 mg/kg, 1 mg/kg, 0.5 mg/kg, 0.3 mg/kg) in comparison with a negative control group (saline administration group). In particular, at 2 doses of 10 mg/kg and 3 mg/kg in the high dose range, prominent survival rate and symptom score-improving effects were exhibited.

TABLE 6

Survival time after preventive administration of antibody D48 (IgG2a) to mice

|  | Dosage (mg/kg) | Survival time after infection (days) | Mean survival time (days) | Significant difference test (vs saline) |
|---|---|---|---|---|
| D48 preventative administration | 10 | 7, >21, >21, >21, >21, >21, >21, >21, >21, >21 | >21 | *** |
|  | 3 | 14, >21, >21, >21, >21, >21, >21, >21, >21, >21 | >21 | *** |
|  | 1 | 5, 7, 7, 8, 8, 8, >21, >21, >21, >21 | 8 | *** |
|  | 0.5 | 6, 6, 6, 6, 6, 7, 7, 8, 8, 8 | 6.5 | ** |
|  | 0.3 | 5, 6, 6, 7, 7, 7, 7, 7, 9, 9 | 7 | ** |
| saline |  | 5, 5, 5, 5, 5, 5, 5, 6, 6, 6 | 5 |  |

*: $p < 0.0001$, : $0.0001 \leq p < 0.001$, *: $0.001 \leq p < 0.05$ (Kaplan-Meier method)

There is a report that HSV moves from the site of infection to ganglia in the body within 48 hours after the entry in therapeutic administration. However, prominent survival rate and symptom score-improving effects were exhibited at 2 doses of 10 mg/kg and 3 mg/kg even in therapeutic administration of antibody D48 at a time point within 48 hours after the infection. From these results, it was confirmed that antibody D48 exhibited a strong infection prevention effect not only in the preventive administration but also in the therapeutic administration.

TABLE 7

Survival time after therapeutic administration of IgG2a of antibody D48 to mice

| | Dosage (mg/kg) | Survival time after infection (days) | Mean survival time (days) | Significant difference test (vs saline) |
|---|---|---|---|---|
| D48 therapeutic administration | 10 | 19, 19, >21, >21, >21, >21, >21, >21, >21 | >21 | *** |
| | 3 | 7, 8, 9, 9, 11, >21, >21, >21, >21, >21 | >16 | *** |
| | 1 | 5, 5, 5, 6, 6, 7, 7, 7, 11, 19 | 6.5 | N.S. |
| | 0.5 | 6, 6, 6, 6, 6, 6, 7, 7, 7, 7 | 6 | N.S. |
| | 0.3 | 5, 6, 6, 6, 7, 7, 7, 7, 8, 8 | 7 | N.S. |
| saline | | 5, 5, 5, 6, 6, 6, 6, 6, 7, 7 | 6 | |

*: $p < 0.0001$, : $0.0001 \leq p < 0.001$, *: $0.001 \leq p < 0.05$ (Kaplan-Meier method)

Example 9 Guinea Pig Infection-Prevention Test

Method of Testing

Using a guinea pig model of genital herpes infection, an infection-prevention test upon preventive administration and therapeutic administration of an anti-HSV gB monoclonal antibody D48 (human-guinea pig chimeric IgG2k) was conducted. Hartley guinea pigs (3 to 5 weeks old, female) purchased from SLC were used. A predetermined amount of the antibody was dissolved in physiological saline for injection and the antibody was intraperitoneally administered at a dose of 1 mg/kg to 30 mg/kg 24 hours before the viral inoculation in the case of preventive administration and 4 days after the viral inoculation in the case of therapeutic administration. In the case of therapeutic administration, symptoms were observed before the administration and individuals exhibiting vaginal symptoms were selected and randomized such that the mean scores of groups are unbiased. The number of animals per group was set at N=9 in the preventive administration and set at N=15 in the therapeutic administration. In the viral inoculation, $5 \times 10^5$ PFU/50 μL of HSV-2 strain MS was transvaginally inoculated under anesthesia and acute phase symptoms were observed for 2 to 3 weeks after the inoculation. The symptom scores were defined as follows: 0: no apparent lesions, 0.5 to 1: erythema, 1.5 to 2: localized vesicles, 2.5 to 3: localized ulcer or crust, 3 to 5: extended vesicles, ulcer, or crust, 3 to 7: extended ulcer or crust with incontinence, 7.5: euthanization due to serious symptoms, and 8: death. Moreover, 7 days after the viral inoculation, vaginal swabs were collected and the amount of virus release was measured by the plaque method. The vagina swabs were collected by inserting a cotton swab wet with the MEM medium into vagina and then wiping the mucosa of the intravaginal wall. Collected vaginal swabs were suspended in 1 mL aliquots of the MEM medium dispensed in siliconized tubes and cryopreserved until use. When measuring the amount of virus release, the vagina swabs were diluted 1-fold, 10-fold, 100-fold, and 1000-fold and inoculated at 100 μL/well onto Vero cells allowed to become full sheets in 96-well or 48-well. Virus adsorption was performed at 37° C. for 1 hour after the inoculation of vaginal swabs and the number of plaques was measured by a predetermined method after culturing in 2% FBS MEM medium supplemented with of 1% methylcellulose for 24 to 72 hours.

Result

Figure 10:
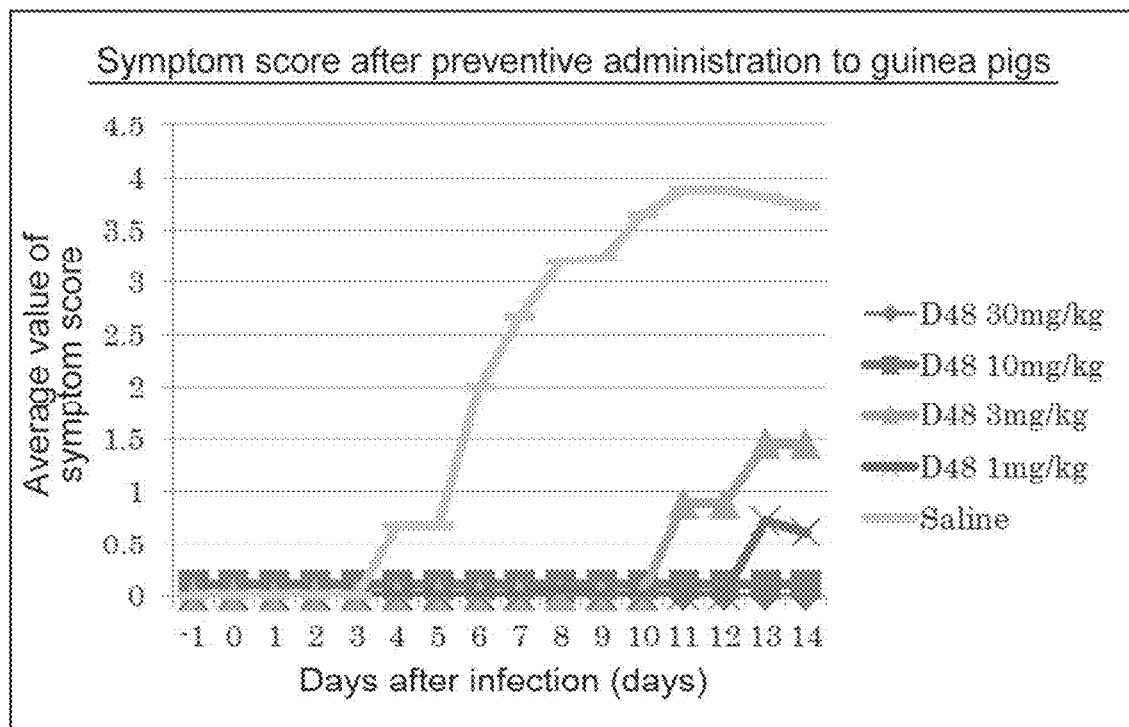
FIG. 10 is a figure illustrating the result of symptom scores after the preventive administration to mice of antibody D48 of Example 9.
Figure 11:
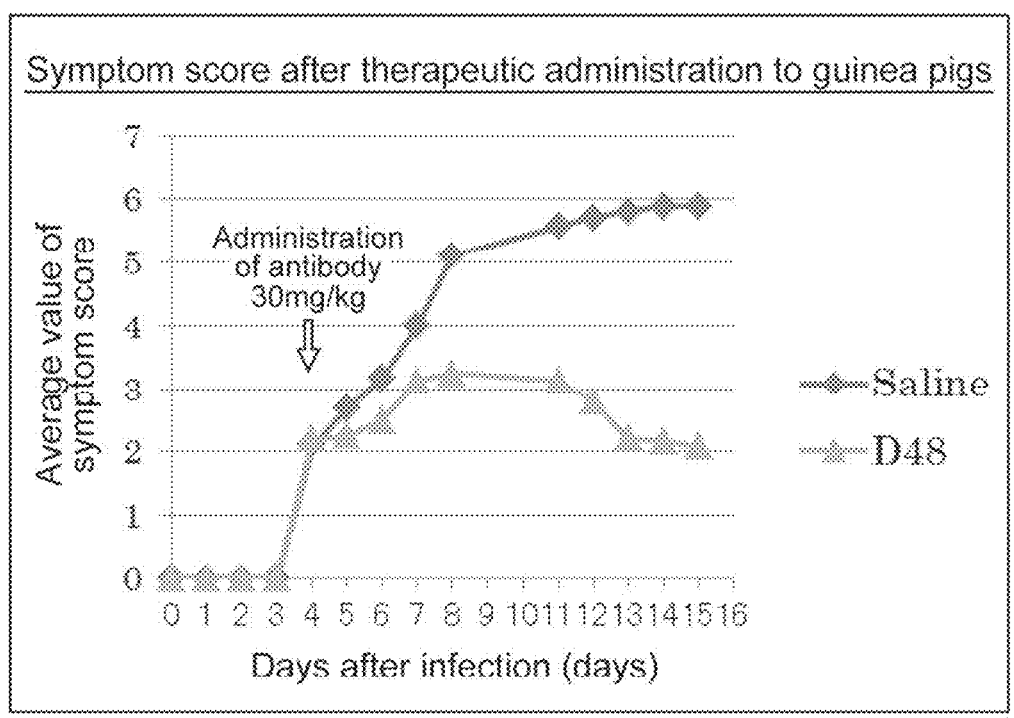
FIG. 11 is a figure illustrating the result of symptom scores after the therapeutic administration to guinea pigs of antibody D48 of Example 9.
Figure 12:
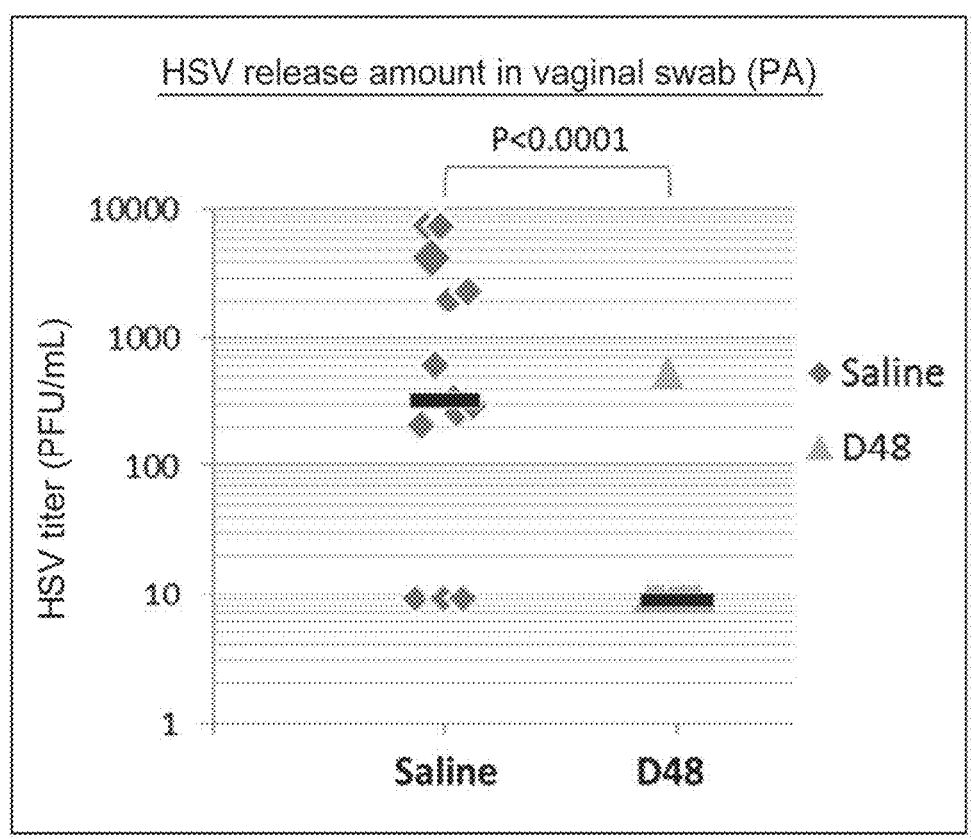
FIG. 12 is a figure illustrating the result of amounts of HSV released in a vaginal swab after the therapeutic administration to guinea pigs of antibody D48 of Example 9.

The result of the symptom score of infection-prevention test of preventive administration of antibody D48 (human-guinea pig chimeric IgG2κ) is shown in FIG. 10, the result of the symptom score of the therapeutic administration infection-prevention test is shown in FIG. 11, and the amount of HSV release in the vaginal swab in the therapeutic administration infection-prevention test using a guinea pig model of genital herpes infection (acute phase) is shown in FIG. 12.

As shown in FIG. 10, after the preventive administration, significant symptom score-improving effect was observed at all doses set (30 mg/kg, 10 mg/kg, 3 mg/kg, 1 mg/kg) in comparison with a negative control group (saline administration group).

As shown in FIG. 11, administration of 30 mg/kg of antibody D48 to guinea pigs which already exhibited vaginal symptoms 4 days after the infection resulted in significant reduction of symptom score in comparison with a negative control group (saline administration group). Moreover, collecting vaginal swabs on Day 7 after the viral inoculation and measuring the amount of virus release by the plaque method resulted in, as shown in FIG. 12, significant reduction of amount of virus release in comparison with a negative control group. Based on the foregoing, it was confirmed that antibody D48 exhibit significant infection prevention effect not only after the preventive administration but also after the therapeutic administration.

INDUSTRIAL APPLICABILITY

According to the present invention, novel anti-HSV gB monoclonal antibodies that exhibit strong HSV-neutralizing effect and can suppress cell to cell spread of HSV can be provided. Thereby, the antibodies can be applied to the prevention and/or the treatment of HSV infection and used as a preventive agent for immunocompromised patients having high risk of HSV infection or patients undergoing bone marrow transplantation, blood stem cell transplantation, or organ transplantation receiving an immunosuppressive agent, as a therapeutic agent for patients undergoing repetitive reactivation of HSV, or as an alternative drug or a concomitant drug of existing antiviral drugs.

The invention claimed is:

1. An anti-HSV gB monoclonal antibody or an antigen-binding fragment thereof against herpes simplex virus (HSV) envelope glycoprotein B (gB), comprising:
   a heavy chain variable region comprising the amino acid sequence set forth in SEQ ID NO: 1 and
   a light chain variable region comprising the amino acid sequence set forth in SEQ ID NO: 2.

2. The anti-HSV gB monoclonal antibody or antigen-binding fragment thereof according to claim 1, wherein the HSV is HSV-1 or HSV-2.

3. A polynucleotide encoding the anti-HSV gB monoclonal antibody or antigen-binding fragment thereof according to claim 1.

4. An expression vector comprising the polynucleotide according to claim 3 and one or more regulatory sequences operably linked to the polynucleotide.

5. A transformant comprising the expression vector according to claim 4 introduced therein.

6. A method for producing an anti-HSV gB monoclonal antibody or antigen-binding fragment thereof using the polynucleotide according to claim 3.

7. A pharmaceutical composition for preventing or treating HSV infection, comprising the anti-HSV gB monoclonal antibody or antigen-binding fragment according to claim 1.

8. The pharmaceutical composition according to claim 7, wherein the HSV infection is HSV-1 infection or HSV-2 infection.

9. The pharmaceutical composition according to claim 7, wherein the HSV infection is selected from the group consisting of herpes labialis, herpetic keratitis, genital herpes, systemic neonatal herpes, and stomatitis, dermatosis, encephalitis, meningitis, and myelitis caused by HSV.

10. An anti-HSV gB monoclonal antibody or an antigen-binding fragment thereof against at least one amino acid residue in the region consisting of the amino acid residues 383-388 of the herpes simplex virus-1 (HSV-1) envelope glycoprotein B (gB) set forth in SEQ ID NO: 10, and/or at least one amino acid residue in the region consisting of the amino acid residues 386-391 of the herpes simplex virus-2 (HSV-2) envelope glycoprotein B (gB) set forth in SEQ ID NO: 11, wherein the anti HSV gB monoclonal antibody or antigen binding fragment thereof comprises:
   a heavy chain variable region comprising the amino acid sequence set forth in SEQ ID NO: 1 and
   a light chain variable region comprising the amino acid sequence set forth in SEQ ID NO: 2.

11. A polynucleotide encoding the anti-HSV gB monoclonal antibody or antigen-binding fragment thereof according to claim 10.

12. An expression vector comprising the polynucleotide according to claim 11 and one or more regulatory sequences operably linked to the polynucleotide.

* * * * *

SEQUENCE LISTING

<160> NUMBER OF SEQ ID NOS: 11

<210> SEQ ID NO 1
<211> LENGTH: 124
<212> TYPE: PRT
<213> ORGANISM: Artificial Sequence
<220> FEATURE:
<223> OTHER INFORMATION: D48 VH

<400> SEQUENCE: 1

Glu Val Gln Leu Val Glu Thr Gly Gly Val Val Arg Pro Gly Arg
1               5                   10                  15

Ser Leu Arg Leu Ser Cys Thr Thr Ser Gly Phe Ser Phe Ser Gly Ser
                20                  25                  30

Ala Met His Trp Val Arg Gln Ala Pro Gly Lys Gly Leu Glu Trp Val
            35                  40                  45

Ala Val Ile Ser His Asp Gly Asn Ile Ile Gln Tyr His Asp Ser Val
        50                  55                  60

Lys Gly Arg Phe Thr Ile Ser Arg Asp Asn Ser Lys Asn Val Leu Leu
65                  70                  75                  80

Leu Gln Met Asn Ser Leu Arg Val Asp Asp Thr Ala Met Tyr Tyr Cys
                85                  90                  95

Ala Arg Asp Val Trp Leu Leu Pro Ala Thr Ile Ser Tyr Ala Phe Asp
            100                 105                 110

Phe Trp Gly Gln Gly Thr Met Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: D48 VL

<400> SEQUENCE: 2

Val Ile Trp Met Thr Gln Ser Pro Pro Ser Leu Ser Ala Ser Ile Gly
1               5                   10                  15

Asp Thr Val Thr Ile Thr Cys Arg Ala Ser Gln Gly Ile Ser Asn Ser
                20                  25                  30

Ile Ala Trp Tyr Gln Arg Pro Gly Lys Ala Pro Glu Leu Leu Val
            35                  40                  45

Tyr Ala Ala Tyr Arg Leu Gln Ser Gly Val Pro Ser Arg Leu Ser Gly
        50                  55                  60

Ser Gly Ser Gly Ala Glu Tyr Thr Leu Thr Ile Lys Asn Met Gln Pro
65                  70                  75                  80

Glu Asp Phe Ala Thr Tyr Tyr Cys Gln Gln Tyr Tyr Asp Asn Pro Leu
                85                  90                  95

Thr Phe Gly Gly Gly Thr Lys Val Glu Ile Lys
            100                 105

<210> SEQ ID NO 3
<211> LENGTH: 6
<212> TYPE: PRT
<213> ORGANISM: Artificial Sequence
<220> FEATURE:

<223> OTHER INFORMATION: D48 VH CRD1

<400> SEQUENCE: 3

Ser Gly Ser Ala Met His
1               5

<210> SEQ ID NO 4
<211> LENGTH: 17
<212> TYPE: PRT
<213> ORGANISM: Artificial Sequence
<220> FEATURE:
<223> OTHER INFORMATION: D48 VH CDR2

<400> SEQUENCE: 4

Val Ile Ser His Asp Gly Asn Ile Ile Gln Tyr His Asp Ser Val Lys
1               5                   10                  15
Gly

<210> SEQ ID NO 5
<211> LENGTH: 15
<212> TYPE: PRT
<213> ORGANISM: Artificial Sequence
<220> FEATURE:
<223> OTHER INFORMATION: D48 VH CDR3

<400> SEQUENCE: 5

Asp Val Trp Leu Leu Pro Ala Thr Ile Ser Tyr Ala Phe Asp Phe
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: D48 VL CDR1

<400> SEQUENCE: 6

Arg Ala Ser Gln Gly Ile Ser Asn Ser Ile Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: D48 VL CDR2

<400> SEQUENCE: 7

Ala Ala Tyr Arg Leu Gln Ser
1               5

<210> SEQ ID NO 8
<211> LENGTH: 9
<212> TYPE: PRT
<213> ORGANISM: Artificial Sequence
<220> FEATURE:
<223> OTHER INFORMATION: D48 VL CDR3

<400> SEQUENCE: 8

Gln Gln Tyr Tyr Asp Asn Pro Leu Thr
1               5

<210> SEQ ID NO 9
<211> LENGTH: 249
<212> TYPE: PRT
<213> ORGANISM: Artificial Sequence
<220> FEATURE:
<223> OTHER INFORMATION: D48 scFv

<400> SEQUENCE: 9

Glu Val Gln Leu Val Glu Thr Gly Gly Gly Val Val Arg Pro Gly Arg
1               5                   10                  15

Ser Leu Arg Leu Ser Cys Thr Thr Ser Gly Phe Ser Phe Ser Gly Ser
            20                  25                  30

Ala Met His Trp Val Arg Gln Ala Pro Gly Lys Gly Leu Glu Trp Val
        35                  40                  45

Ala Val Ile Ser His Asp Gly Asn Ile Ile Gln Tyr His Asp Ser Val
    50                  55                  60

Lys Gly Arg Phe Thr Ile Ser Arg Asp Asn Ser Lys Asn Val Leu Leu
65                  70                  75                  80

Leu Gln Met Asn Ser Leu Arg Val Asp Asp Thr Ala Met Tyr Tyr Cys
                85                  90                  95

Ala Arg Asp Val Trp Leu Leu Pro Ala Thr Ile Ser Tyr Ala Phe Asp
            100                 105                 110

Phe Trp Gly Gln Gly Thr Met Val Thr Val Ser Ser Ala Ser Thr Gly
        115                 120                 125

Gly Gly Gly Ser Gly Gly Gly Gly Ser Gly Gly Gly Gly Ser Val Ile
    130                 135                 140

Trp Met Thr Gln Ser Pro Pro Ser Leu Ser Ala Ser Ile Gly Asp Thr
145                 150                 155                 160

Val Thr Ile Thr Cys Arg Ala Ser Gln Gly Ile Ser Asn Ser Ile Ala
                165                 170                 175

Trp Tyr Gln Arg Arg Pro Gly Lys Ala Pro Glu Leu Leu Val Tyr Ala
            180                 185                 190

Ala Tyr Arg Leu Gln Ser Gly Val Pro Ser Arg Leu Ser Gly Ser Gly
        195                 200                 205

Ser Gly Ala Glu Tyr Thr Leu Thr Ile Lys Asn Met Gln Pro Glu Asp
    210                 215                 220

Phe Ala Thr Tyr Tyr Cys Gln Gln Tyr Tyr Asp Asn Pro Leu Thr Phe
225                 230                 235                 240

Gly Gly Gly Thr Lys Val Glu Ile Lys
                245

<210> SEQ ID NO 10
<211> LENGTH: 874
<212> TYPE: PRT
<213> ORGANISM: Herpes simplex virus 1

<400> SEQUENCE: 10

Ala Pro Thr Ser Pro Gly Thr Pro Gly Val Ala Ala Ala Thr Gln Ala
1               5                   10                  15

Ala Asn Gly Gly Pro Ala Thr Pro Ala Pro Pro Leu Gly Ala Ala
            20                  25                  30

Pro Thr Gly Asp Pro Lys Pro Lys Lys Asn Lys Lys Pro Lys Asn Pro
        35                  40                  45

Thr Pro Pro Arg Pro Ala Gly Asp Asn Ala Thr Val Ala Ala Gly His
    50                  55                  60

Ala Thr Leu Arg Glu His Leu Arg Asp Ile Lys Ala Glu Asn Thr Asp
65                  70                  75                  80

Ala Asn Phe Tyr Val Cys Pro Pro Pro Thr Gly Ala Thr Val Val Gln
                85                  90                  95

```
Phe Glu Gln Pro Arg Arg Cys Pro Thr Arg Pro Glu Gly Gln Asn Tyr
            100                 105                 110
Thr Glu Gly Ile Ala Val Val Phe Lys Glu Asn Ile Ala Pro Tyr Lys
        115                 120                 125
Phe Lys Ala Thr Met Tyr Tyr Lys Asp Val Thr Val Ser Gln Val Trp
    130                 135                 140
Phe Gly His Arg Tyr Ser Gln Phe Met Gly Ile Phe Glu Asp Arg Ala
145                 150                 155                 160
Pro Val Pro Phe Glu Glu Val Ile Asp Lys Ile Asn Ala Lys Gly Val
                165                 170                 175
Cys Arg Ser Thr Ala Lys Tyr Val Arg Asn Asn Leu Glu Thr Thr Ala
            180                 185                 190
Phe His Arg Asp Asp His Glu Thr Asp Met Glu Leu Lys Pro Ala Asn
        195                 200                 205
Ala Ala Thr Arg Thr Ser Arg Gly Trp His Thr Thr Asp Leu Lys Tyr
    210                 215                 220
Asn Pro Ser Arg Val Glu Ala Phe His Arg Tyr Gly Thr Thr Val Asn
225                 230                 235                 240
Cys Ile Val Glu Glu Val Asp Ala Arg Ser Val Tyr Pro Tyr Asp Glu
                245                 250                 255
Phe Val Leu Ala Thr Gly Asp Phe Val Tyr Met Ser Pro Phe Tyr Gly
            260                 265                 270
Tyr Arg Glu Gly Ser His Thr Glu His Thr Thr Tyr Ala Ala Asp Arg
        275                 280                 285
Phe Lys Gln Val Asp Gly Phe Tyr Ala Arg Asp Leu Thr Thr Lys Ala
    290                 295                 300
Arg Ala Thr Ala Pro Thr Thr Arg Asn Leu Leu Thr Thr Pro Lys Phe
305                 310                 315                 320
Thr Val Ala Trp Asp Trp Val Pro Lys Arg Pro Ser Val Cys Thr Met
                325                 330                 335
Thr Lys Trp Gln Glu Val Asp Glu Met Leu Arg Ser Glu Tyr Gly Gly
            340                 345                 350
Ser Phe Arg Phe Ser Ser Asp Ala Ile Ser Thr Thr Phe Thr Thr Asn
        355                 360                 365
Leu Thr Glu Tyr Pro Leu Ser Arg Val Asp Leu Gly Asp Cys Ile Gly
    370                 375                 380
Lys Asp Ala Arg Asp Ala Met Asp Arg Ile Phe Ala Arg Arg Tyr Asn
385                 390                 395                 400
Ala Thr His Ile Lys Val Gly Gln Pro Gln Tyr Tyr Gln Ala Asn Gly
                405                 410                 415
Gly Phe Leu Ile Ala Tyr Gln Pro Leu Leu Ser Asn Thr Leu Ala Glu
            420                 425                 430
Leu Tyr Val Arg Glu His Leu Arg Glu Gln Ser Arg Lys Pro Pro Asn
        435                 440                 445
Pro Thr Pro Pro Pro Gly Ala Ser Ala Asn Ala Ser Val Glu Arg
    450                 455                 460
Ile Lys Thr Thr Ser Ser Ile Glu Phe Ala Arg Leu Gln Phe Thr Tyr
465                 470                 475                 480
Asn His Ile Gln Arg His Val Asn Asp Met Leu Gly Arg Val Ala Ile
                485                 490                 495
Ala Trp Cys Glu Leu Gln Asn His Glu Leu Thr Leu Trp Asn Glu Ala
            500                 505                 510
```

```
Arg Lys Leu Asn Pro Asn Ala Ile Ala Ser Val Thr Val Gly Arg Arg
        515                 520                 525

Val Ser Ala Arg Met Leu Gly Asp Val Met Ala Val Ser Thr Cys Val
530                 535                 540

Pro Val Ala Ala Asp Asn Val Ile Val Gln Asn Ser Met Arg Ile Ser
545                 550                 555                 560

Ser Arg Pro Gly Ala Cys Tyr Ser Arg Pro Leu Val Ser Phe Arg Tyr
                565                 570                 575

Glu Asp Gln Gly Pro Leu Val Glu Gly Gln Leu Gly Glu Asn Asn Glu
            580                 585                 590

Leu Arg Leu Thr Arg Asp Ala Ile Glu Pro Cys Thr Val Gly His Arg
        595                 600                 605

Arg Tyr Phe Thr Phe Gly Gly Tyr Val Tyr Phe Glu Glu Tyr Ala
    610                 615                 620

Tyr Ser His Gln Leu Ser Arg Ala Asp Ile Thr Thr Val Ser Thr Phe
625                 630                 635                 640

Ile Asp Leu Asn Ile Thr Met Leu Glu Asp His Glu Phe Val Pro Leu
                645                 650                 655

Glu Val Tyr Thr Arg His Glu Ile Lys Asp Ser Gly Leu Leu Asp Tyr
            660                 665                 670

Thr Glu Val Gln Arg Arg Asn Gln Leu His Asp Leu Arg Phe Ala Asp
        675                 680                 685

Ile Asp Thr Val Ile His Ala Asp Ala Asn Ala Ala Met Phe Ala Gly
690                 695                 700

Leu Gly Ala Phe Phe Glu Gly Met Gly Asp Leu Gly Arg Ala Val Gly
705                 710                 715                 720

Lys Val Val Met Gly Ile Val Gly Gly Val Val Ser Ala Val Ser Gly
                725                 730                 735

Val Ser Ser Phe Met Ser Asn Pro Phe Gly Ala Leu Ala Val Gly Leu
            740                 745                 750

Leu Val Leu Ala Gly Leu Ala Ala Ala Phe Phe Ala Phe Arg Tyr Val
        755                 760                 765

Met Arg Leu Gln Ser Asn Pro Met Lys Ala Leu Tyr Pro Leu Thr Thr
770                 775                 780

Lys Glu Leu Lys Asn Pro Thr Asn Pro Asp Ala Ser Gly Glu Gly Glu
785                 790                 795                 800

Glu Gly Gly Asp Phe Asp Glu Ala Lys Leu Ala Glu Ala Arg Glu Met
                805                 810                 815

Ile Arg Tyr Met Ala Leu Val Ser Ala Met Glu Arg Thr Glu His Lys
            820                 825                 830

Ala Lys Lys Lys Gly Thr Ser Ala Leu Leu Ser Ala Lys Val Thr Asp
        835                 840                 845

Met Val Met Arg Lys Arg Arg Asn Thr Asn Tyr Thr Gln Val Pro Asn
850                 855                 860

Lys Asp Gly Asp Ala Asp Glu Asp Asp Leu
865                 870
```

<210> SEQ ID NO 11
<211> LENGTH: 882
<212> TYPE: PRT
<213> ORGANISM: Herpes simplex virus-2

<400> SEQUENCE: 11

```
Ala Pro Ala Ala Pro Ala Ala Pro Arg Ala Ser Gly Gly Val Ala Ala
1               5                   10                  15

Thr Val Ala Ala Asn Gly Gly Pro Ala Ser Arg Pro Pro Val Pro
            20                  25                  30

Ser Pro Ala Thr Thr Lys Ala Arg Lys Arg Lys Thr Lys Lys Pro Pro
            35                  40                  45

Lys Arg Pro Glu Ala Thr Pro Pro Asp Ala Asn Ala Thr Val Ala
    50                  55                  60

Ala Gly His Ala Thr Leu Arg Ala His Leu Arg Glu Ile Lys Val Glu
65                  70                  75                  80

Asn Ala Asp Ala Gln Phe Tyr Val Cys Pro Pro Thr Gly Ala Thr
                85                  90                  95

Val Val Gln Phe Glu Gln Pro Arg Arg Cys Pro Thr Arg Pro Glu Gly
            100                 105                 110

Gln Asn Tyr Thr Glu Gly Ile Ala Val Val Phe Lys Glu Asn Ile Ala
            115                 120                 125

Pro Tyr Lys Phe Lys Ala Thr Met Tyr Tyr Lys Asp Val Thr Val Ser
    130                 135                 140

Gln Val Trp Phe Gly His Arg Tyr Ser Gln Phe Met Gly Ile Phe Glu
145                 150                 155                 160

Asp Arg Ala Pro Val Pro Phe Glu Glu Val Ile Asp Lys Ile Asn Ala
                165                 170                 175

Lys Gly Val Cys Arg Ser Thr Ala Lys Tyr Val Arg Asn Asn Met Glu
            180                 185                 190

Thr Thr Ala Phe His Arg Asp Asp His Glu Thr Asp Met Glu Leu Lys
            195                 200                 205

Pro Ala Lys Val Ala Thr Arg Thr Ser Arg Gly Trp His Thr Thr Asp
    210                 215                 220

Leu Lys Tyr Asn Pro Ser Arg Val Glu Ala Phe His Arg Tyr Gly Thr
225                 230                 235                 240

Thr Val Asn Cys Ile Val Glu Glu Val Asp Ala Arg Ser Val Tyr Pro
                245                 250                 255

Tyr Asp Glu Phe Val Leu Ala Thr Gly Asp Phe Val Tyr Met Ser Pro
            260                 265                 270

Phe Tyr Gly Tyr Arg Glu Gly Ser His Thr Glu His Thr Ser Tyr Ala
            275                 280                 285

Ala Asp Arg Phe Lys Gln Val Asp Gly Phe Tyr Ala Arg Asp Leu Thr
    290                 295                 300

Thr Lys Ala Arg Ala Thr Ser Pro Thr Thr Arg Asn Leu Leu Thr Thr
305                 310                 315                 320

Pro Lys Phe Thr Val Ala Trp Asp Trp Val Pro Lys Arg Pro Ala Val
                325                 330                 335

Cys Thr Met Thr Lys Trp Gln Glu Val Asp Glu Met Leu Arg Ala Glu
            340                 345                 350

Tyr Gly Gly Ser Phe Arg Phe Ser Ser Asp Ala Ile Ser Thr Thr Phe
            355                 360                 365

Thr Thr Asn Leu Thr Gln Tyr Ser Leu Ser Arg Val Asp Leu Gly Asp
    370                 375                 380

Cys Ile Gly Arg Asp Ala Arg Glu Ala Ile Asp Arg Met Phe Ala Arg
385                 390                 395                 400
```

```
Lys Tyr Asn Ala Thr His Ile Lys Val Gly Gln Pro Gln Tyr Tyr Leu
                405                 410                 415
Ala Thr Gly Gly Phe Leu Ile Ala Tyr Gln Pro Leu Leu Ser Asn Thr
            420                 425                 430
Leu Ala Glu Leu Tyr Val Arg Glu Tyr Met Arg Glu Gln Asp Arg Lys
        435                 440                 445
Pro Arg Asn Ala Thr Pro Ala Pro Leu Arg Glu Ala Pro Ser Ala Asn
    450                 455                 460
Ala Ser Val Glu Arg Ile Lys Thr Thr Ser Ser Ile Glu Phe Ala Arg
465                 470                 475                 480
Leu Gln Phe Thr Tyr Asn His Ile Gln Arg His Val Asn Asp Met Leu
                485                 490                 495
Gly Arg Ile Ala Val Ala Trp Cys Glu Leu Gln Asn His Glu Leu Thr
            500                 505                 510
Leu Trp Asn Glu Ala Arg Lys Leu Asn Pro Asn Ala Ile Ala Ser Ala
        515                 520                 525
Thr Val Gly Arg Arg Val Ser Ala Arg Met Leu Gly Asp Val Met Ala
    530                 535                 540
Val Ser Thr Cys Val Pro Val Ala Pro Asp Asn Val Ile Val Gln Asn
545                 550                 555                 560
Ser Met Arg Val Ser Ser Arg Pro Gly Thr Cys Tyr Ser Arg Pro Leu
                565                 570                 575
Val Ser Phe Arg Tyr Glu Asp Gln Gly Pro Leu Ile Glu Gly Gln Leu
            580                 585                 590
Gly Glu Asn Asn Glu Leu Arg Leu Thr Arg Asp Ala Leu Glu Pro Cys
        595                 600                 605
Thr Val Gly His Arg Arg Tyr Phe Ile Phe Gly Gly Gly Tyr Val Tyr
    610                 615                 620
Phe Glu Glu Tyr Ala Tyr Ser His Gln Leu Ser Arg Ala Asp Val Thr
625                 630                 635                 640
Thr Val Ser Thr Phe Ile Asp Leu Asn Ile Thr Met Leu Glu Asp His
                645                 650                 655
Glu Phe Val Pro Leu Glu Val Tyr Thr Arg His Glu Ile Lys Asp Ser
            660                 665                 670
Gly Leu Leu Asp Tyr Thr Glu Val Gln Arg Arg Asn Gln Leu His Asp
        675                 680                 685
Leu Arg Phe Ala Asp Ile Asp Thr Val Ile Arg Ala Asp Ala Asn Ala
    690                 695                 700
Ala Met Phe Ala Gly Leu Cys Ala Phe Phe Glu Gly Met Gly Asp Leu
705                 710                 715                 720
Gly Arg Ala Val Gly Lys Val Val Met Gly Val Val Gly Gly Val Val
                725                 730                 735
Ser Ala Val Ser Gly Val Ser Ser Phe Met Ser Asn Pro Phe Gly Ala
            740                 745                 750
Leu Ala Val Gly Leu Leu Val Leu Ala Gly Leu Val Ala Ala Phe Phe
        755                 760                 765
Ala Phe Arg Tyr Val Leu Gln Leu Gln Arg Asn Pro Met Lys Ala Leu
    770                 775                 780
Tyr Pro Leu Thr Thr Lys Glu Leu Lys Thr Ser Asp Pro Gly Gly Val
785                 790                 795                 800
Gly Gly Glu Gly Glu Glu Gly Ala Glu Gly Gly Phe Asp Glu Ala
                805                 810                 815
```

```
Lys Leu Ala Glu Ala Arg Glu Met Ile Arg Tyr Met Ala Leu Val Ser
            820                 825                 830

Ala Met Glu Arg Thr Glu His Lys Ala Arg Lys Lys Gly Thr Ser Ala
        835                 840                 845

Leu Leu Ser Ser Lys Val Thr Asn Met Val Leu Arg Lys Arg Asn Lys
    850                 855                 860

Ala Arg Tyr Ser Pro Leu His Asn Glu Asp Glu Ala Gly Asp Glu Asp
865                 870                 875                 880

Glu Leu
```